US012226546B2

United States Patent
Deming et al.

(10) Patent No.: US 12,226,546 B2
(45) Date of Patent: Feb. 18, 2025

(54) POLYION COMPLEX POLYPEPTIDE HYDROGELS AND USES THEREOF

(71) Applicant: The Regents of the University of California, Oakland, CA (US)

(72) Inventors: Timothy J. Deming, Los Angeles, CA (US); Yintao Sun, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/651,813

(22) PCT Filed: Sep. 27, 2018

(86) PCT No.: PCT/US2018/053050
§ 371 (c)(1),
(2) Date: Mar. 27, 2020

(87) PCT Pub. No.: WO2019/067676
PCT Pub. Date: Apr. 4, 2019

(65) Prior Publication Data
US 2020/0246503 A1 Aug. 6, 2020

Related U.S. Application Data

(60) Provisional application No. 62/564,765, filed on Sep. 28, 2017.

(51) Int. Cl.
*A61L 27/22* (2006.01)
*A61K 47/42* (2017.01)
(Continued)

(52) U.S. Cl.
CPC .............. *A61L 27/22* (2013.01); *A61L 27/52* (2013.01); *A61K 9/06* (2013.01); *A61K 47/42* (2013.01)

(58) Field of Classification Search
CPC ........ A61K 31/785; A61K 47/42; A61K 9/06; A61L 27/22; A61L 27/52; C07K 14/001
See application file for complete search history.

(56) References Cited

U.S. PATENT DOCUMENTS 4,554,101 A * 11/1985 Hopp .................. C07K 14/005
424/257.1
5,670,483 A * 9/1997 Zhang ..................... C07K 7/08
530/300

(Continued)

FOREIGN PATENT DOCUMENTS

WO    WO-01/94379 A2    12/2001
WO    WO-2006/113667 A1    10/2006
(Continued)

OTHER PUBLICATIONS

Livingstone et al., Protein sequence alignments, CABIOS, vol. 9(6):745-756 (1993) (Year: 1993).*

(Continued)

*Primary Examiner* — Randall L Beane
(74) *Attorney, Agent, or Firm* — Foley Hoag LLP; David P. Halstead; Janine S. Ladislaw

(57) ABSTRACT

Described herein are compositions comprising at least two diblock copolypeptides, wherein each copolypeptide has an ionic segment with the opposite charge from the other. The copolypeptides form β-sheet structured hydrogel assemblies via polyion complexation when mixed in aqueous media. As a result of their unique physical properties, the hydrogels are useful as cell suspension or cell culture media, in drug or cell delivery systems, in scaffolds for tissue repair, or as 3d-printable media.

21 Claims, 10 Drawing Sheets

Specification includes a Sequence Listing.

(51) Int. Cl.
*A61L 27/52* (2006.01)
*A61K 9/06* (2006.01)

(56) References Cited

U.S. PATENT DOCUMENTS

| | | | |
|---|---|---|---|
| 5,856,308 A | 1/1999 | St. Pierre et al. | |
| 6,361,768 B1 | 3/2002 | Galleguillos et al. | |
| 6,686,446 B2 | 2/2004 | Deming et al. | |
| 7,279,458 B2 | 10/2007 | Fatheree et al. | |
| 7,846,445 B2* | 12/2010 | Schellenberger | C07K 14/475 424/179.1 |
| 8,691,204 B2 | 4/2014 | Deming et al. | |
| 9,017,730 B2 | 4/2015 | Bevilacqua et al. | |
| 10,448,634 B2 | 10/2019 | Bevilacqua et al. | |
| 2002/0032309 A1 | 3/2002 | Deming et al. | |
| 2003/0147958 A1 | 8/2003 | Ahn et al. | |
| 2003/0176335 A1* | 9/2003 | Zhang | C07K 14/001 514/1.2 |
| 2005/0031522 A1 | 2/2005 | Delaney et al. | |
| 2005/0042753 A1 | 2/2005 | Yang et al. | |
| 2005/0079159 A1 | 4/2005 | Shastri et al. | |
| 2006/0240092 A1 | 10/2006 | Breitenkamp et al. | |
| 2007/0099840 A1* | 5/2007 | Ulijn | A61K 47/42 514/29 |
| 2007/0157967 A1* | 7/2007 | Mershin | B82Y 10/00 136/263 |
| 2007/0190110 A1 | 8/2007 | Pameijer et al. | |
| 2008/0003288 A1 | 1/2008 | Bromberg et al. | |
| 2008/0125581 A1 | 5/2008 | Deming et al. | |
| 2008/0166388 A1 | 7/2008 | Palecek et al. | |
| 2008/0176807 A1 | 7/2008 | DeGrado et al. | |
| 2008/0243049 A1 | 10/2008 | Hardy | |
| 2009/0028832 A1* | 1/2009 | Chung | A61P 35/00 424/93.7 |
| 2009/0105341 A1* | 4/2009 | Stanton | C12P 7/6472 435/243 |
| 2009/0175785 A1* | 7/2009 | Gazit | A61L 27/227 424/9.1 |
| 2009/0208548 A1 | 8/2009 | Mason et al. | |
| 2010/0003336 A1 | 1/2010 | Deming et al. | |
| 2010/0222407 A1 | 9/2010 | Segura et al. | |
| 2012/0093722 A1 | 4/2012 | Deming et al. | |
| 2012/0178676 A1* | 7/2012 | Barrack | C07K 14/62 514/21.3 |
| 2013/0202711 A1* | 8/2013 | Kataoka | B01J 13/14 424/496 |
| 2014/0286865 A1* | 9/2014 | Deming | A61K 9/0085 514/17.7 |
| 2015/0258219 A1* | 9/2015 | Kataoka | C08G 69/40 424/9.42 |
| 2016/0002405 A1* | 1/2016 | Deming | A61K 9/1273 525/420 |
| 2020/0246503 A1 | 8/2020 | Deming et al. | |
| 2021/0330795 A1 | 10/2021 | Deming et al. | |

FOREIGN PATENT DOCUMENTS

| | | |
|---|---|---|
| WO | WO-2008/070571 A2 | 6/2008 |
| WO | WO-2009/025802 A1 | 2/2009 |
| WO | WO-2010/096572 A2 | 8/2010 |
| WO | WO-2012/027411 A2 | 3/2012 |
| WO | WO-2014/134203 A1 | 9/2014 |
| WO | WO-2020/198644 A1 | 10/2020 |

OTHER PUBLICATIONS

William R. Taylor, 5—The properties of Amino Acids in Sequences, In Biological Techniques Series, Genetic Databases, Academic Press, 1997, pp. 81-103, ISSN 08924473 (Year: 1997).*
Wagner et al., New Naturally Occurring Amino Acids, Angew. Chem. Int. Ed. Engl., vol. 22:816-828 (1983) (Year: 1983).*
Cui et al., High performance and reversible ionic polypeptide hydrogel based on charge-driven assembly for biomedical applications , Acta Biomaterialia, vol. 11:183-190 (2015) (Year: 2015).*
Strohl, Fusion Proteins for Half-Life Extension of Biologics as a Strategy to Make Biobetters, BioDrugs, vol. 29:215-239 (2015) (Year: 2015).*
Harada et al., Formation of Polyion Complex Micelles in an Aqueous Milieu from a Pair of Oppositely-Charged Block Copolymers with Poly(ethylene glycol) Segments, Macromolecules, vol. 28:5294-5299 (1995) (Year: 1995).*
Insua et al., Polyion complex (PIC) particles: Preparation and biomedical applications, European Polymer Journal, vol. 81:198-215 (Jun. 2016) (Year: 2016).*
Srivastava et al., Gel phase formation in dilute triblock copolyelectrolyte complexes, Nature Communications, vol. 8:14131. doi: 10.1038/ncomms14131, 9 pages (Feb. 23, 2017) (Year: 2017).*
Kishimura, Development of polyion complex vesicles (PICsomes) from block copolymers for biomedical applications, Polymers Journal, vol. 45:892-897 (Apr. 2013) (Year: 2013).*
Pitha et al., Poly-L-methionine Sulfoxide: A biologically Inert Analogue of Dimethyl Sulfoxide with Solubilizing Potency, Journal of Pharmaceutical Sciences, vol. 72(6):665-668 (1983) (Year: 1983).*
Deming et al., Synthesis of Side-Chain Modified Polypeptides, Chem. Rev., vol. 116:786-808 (Jul. 6, 2015) (Year: 2015).*
Papadakis et al., Responsive Hydrogels from Associative Block Copolymers: Physical Gelling through Polyion Complexation. Gels. Jan. 1, 2017;3(1):3. doi: 10.3390/gels3010003; PMID: 30920500; PMCID: PMC6318663 (Year: 2017).*
Krogstad et al., Effects of Polymer and Salt Concentration on the Structure and Properties of Triblock Copolymer Coacervate Hydrogels, Macromolecules, vol. 46(4):1512-1518 (Feb. 6, 2013) (Year: 2013).*
Schellenberger et al., A recombinant polypeptide extends the in vivo half-life of peptides and proteins in a tunable manner, Nature Biotechnology, vol. 27(2):1186-1190 with 21 pages of Supplemental Online material (Nov. 15, 2009) (Year: 2009).*
Jenkins et al., "Glossary of basic terms in polymer science (IUPAC Recommendations 1996)" Pure and Applied Chemistry, vol. 68, No. 12, 1996, pp. 2287-2311. https://doi.org/10.1351/pac199668122287 (Year: 1996).*
Extended European Search Report for EP Application No. 18861462.2 dated Aug. 23, 2021.
Carlsen et al., "Self-assembly of polypeptide-based block copolymer amphiphiles," Current Opinion in Colloid & Interface Science, 14(5):329-339 (2009).
U.S. Appl. No. 17/598,761, Pending.
U.S. Appl. No. 17/238,632, Pending.
U.S. Appl. No. 16/651,813, Pending.
International Search Report and Written Opinion for International Application No. PCT/US2020/025377 dated Jul. 16, 2020.
Tian et al., "Polypeptide based vesicles: formation, properties and application for drug delivery," Journal of Materials Chemistry, 22(34):17404-17414 (2012).
Xu et al., "Amphiphilic poly (amino acid) based micelles applied to drug delivery: The in vitro and in vivo challenges and the corresponding potential strategies," Journal of Controlled Release, 199:84-97 (2014).
Arunan et al., "Definition of the hydrogen bond (IUPAC Recommendations 2011)," Pure Appl. Chem., 83(8): 1637-1641 (Jul. 2011).
Captain et al., "Methionine sulfoxide and phosphonate containing double hydrophilic block copolypeptides and their mineralization of calcium carbonate," Journal of Polymer Science Part A: Polymer Chemistry, 54(23): 3707-3712 (Sep. 7, 2016).
Chassenieux et al., "Recent trends in pH/thermo-responsive self-assembling hydrogels: from polyions to peptide-based polymeric gelators," Soft Matter, 12(5):1344-1359 (Jan. 5, 2016).
Xu et al., "Thermosensitive Polypeptide Hydrogels as a platform for ROS-triggered cargo release with innate cytoprotective ability under oxidative stress," Advanced Healthcare Materials, 5(1): 1979-1990 (Jun. 10, 2016).
Yinato Sun., "Study of Polyion Complex Structure Formation from Mixing Oppositely-Charged Block Copolypeptides," Dissertation for Degree of Docket of Philosophy in Bioengineering, University of California Los Angeles: 132 pages (Apr. 19, 2019).

(56) References Cited

OTHER PUBLICATIONS

AU 2011 293468 Examination Report dated Dec. 10, 2013.
Bani-Jaber et al., "Efficacy of the antimicrobial peptide nisin in emulsifying oil in water," J Food Sci, 65(3):502-6 (2000).
Bellomo et al., "Stimuli-responsive polypeptide vesicles by conformation-specific assembly," Nat Mater 3:244-248 (2004).
Bermudez et al., "Molecular weight dependence of polymersome membrane structure, elasticity, and stability," Macromol, 35:8203-8 (2002).
Boateng et al., "Wound Healing Dressings and Drug Delivery Systems: A Review," J Pharm Sci, 97(8):2892-2923 (2008).
Boyce et al., "Guideline for hand hygiene in health-care settings," Morbidity and Mortality Weekly Report, 51(RR-16):1-54 (2002).
Brogden et al., "Antimicrobial peptides: Pore formers or metabolic inhibitors in bacteria?" Nat Rev Microbiol, 3(3):238-50 (2005).
Brooks et al., "Tat peptide-mediated cellular delivery: back to basics," Adv Drug Deliv Rev, 57:559-77 (2005).
CA 2,809,093 Examination Report dated Mar. 31, 2014.
Calnan et al., "Arginine-mediated RNA recognition: the arginine fork," Science, 252:1167-71 (1991).
CN 201180051224 Examination Report datd May 8, 2014.
Deming et al., "Methodologies for preparation of synthetic block copolypeptides: Materials with future promise in drug delivery," Adv Drug Deliver Rev, 54:1145-55 (2002).
Deming et al., "Polypeptide and polypeptide hybrid copolymer synthesis via NCA polymerization," ChemInform, 38(5):1-18 (2007).
Deming et al., "Synthetic polypeptides for biomedical applications," Prog Polym Sci, 32:858-75 (2007).
Deming, "Cobalt and iron initiators for the controlled polymerization of alpha-amino acid-N-carboxyhanhydrides," Macromol, 32:4500-2 (1999).
Deming, "Facile synthesis of block copolypeptides of defined architecture," Nature, 390:386-9 (1997).
Discher et al., "A. Polymer vesicles," Science, 297:967-73 (2002).
Discher et al., "Polymer vesicles in various media," Curr Opin Coll Interface Sci, 5:125-45 (2000).
Dondoni et al., "The emergence of thiol-ene coupling as a click process for materials and bioorganic chemistry," Angew Chem Int Ed Engl., 47(47):8995-7 (2008).
Eberlein et al., "Clinical use of polihexanide on acute and chronic wounds for antisepsis and docontamination," Skin Pharmacol Physiol, 23(Suppl.):45-51 (2010).
Epand et al., "Dual mechanism of bacterial lethality for a cationic sequence-random copolymer that mimics host-defense antimicrobial peptides," J Mol Biol, 379(1):38-50 (2008).
Extended European Search Report dated Nov. 9, 2012 in European Application No. 10744302.0.
Futaki, "Membrane-permeable arginine-rich peptides and the translocation mechanisms," Adv Drug Deliv Rev, 57:547-58 (2005).
Gabriel et al., "Infectious Disease: Connecting innate immunity to biocidal polymers," Mater Sci Eng R Rep, 57(1-6):28-64 (2007).
Gilbert et al., "Cationic antiseptics: Diversity of action under a common epithet," J Applied Microbiol, 99(4):703-15 (2005).
Ginsburg et al., "Action of polylysine on the fibrinolytic reaction," Bulletin of the Research Council of Israel, 4:51-6 (1954).
Goodson et al., "Characterization of novel antimicrobial peptoids," Antimicrob Agents Chemother, 43(6):1429-34 (1999).
Hancock et al., "Cationic peptides: A new source of antibiotics," Trends Biotechnol, 16(2):82-8 (1998).
Hanson et al., "Nanoscale double emulsions stabilized by single-component block copolypeptides," Nature, 455:85-9 (2008).
Higgins et al., "Resistance to antibiotics and biocides among non-fermenting gram-negative bacteria," Clin Microbiol Infections, 7:308-15 (2001).
Ho et al., "Improving emulsifying activity of [var epsilon]-polylysine by conjugation with dextran through the Maillard reaction," Food Chem, 68(4):449-55 (2000).
Holowka et al., "Charged polypeptide vesicles with controllable diameter," J Am Chem Soc, 127(35):12423-8 (2005).
Hou et al., "The repair of brain lesion by implamantation of hyaluronic acid hydrogels modified with laminin," J Neurosci Meth, 148(1):60-70 (2005).
Ilker et al., "Tuning the hemolytic and antibacterial activities of amphiphilic polynorbornene derivatives," J Am Chem Soc, 126(48):15870-5 (2004).
Indian Office Action dated Feb. 22, 2013 issued in Application No. 1231/mumnp/2009.
International Search Report and a Written Opinion of the International Searching Authority issued in Application No. PCT/US2010/24603, dated Sep. 28, 2010.
International Search Report and Written Opinion for International Application No. PCT/US2018/053050 dated Jan. 21, 2019.
International Search Report and Written Opinion issued by the International Searching Authority in corresponding International Application No. PCT/US2011/048869, dated Mar. 28, 2012.
International Search Report issued in PCT Application No. PCT/US2011/048869 dated Sep. 28, 2012.
Japanese Office Action dated Nov. 27, 2012, issued in Japanese Patent Application No. 2009-539522.
Jenkins et al., "Interactions of polylysine with platelets," Blood, 37(4):395-412 (1971).
JP 2013-526108 Examination Report dated Jun. 10, 2014.
Kar et al., "Synthesis and characterization of poly-L-lysine-grafted silica nanoparticles synthesized via NCA polymerization and click chemistry," Langmuir, 26(8):5772-81 (2010).
Kim et al., "Pharmacodynamics of insulin in polyethylene glycol-coated liposomes," Int J Pharm, 180:75-81 (1999).
Kuroda et al., "The role of hydrophobicity in the antimicrobial and hemolytic activities of polymethacrylate derivatives," Chem, 15(5):1123-33 (2009).
Lam et al., "D-amino acids govern stationary phase cell wall remodeling in bacteria," Science, 325(5947):1552-5 (2009).
Landman et al., "Polymyxins revisited," Clin Microbiol Rev, 21(3):449-65 (2008).
Lin et al., "Chondroitinase ABC has a long-lasting effect on chondroitin sulphate glycosaminoglycan content in the injured rat brain," J Neurochem, 104(2):400-8 (2008).
Lio et al., "Topical antibacterial agents," Infect Dis Clin N Am, 23(4):945-63 (2009).
Liu et al., "De novo design, synthesis, and characterization of antimicrobial beta-peptides," J Am Chem Soc, 123(31):7553-9 (2001).
Liu et al., "Nontoxic membrane-active antimicrobial arylamide oligomers," Angew Chem Int Ed Engl, 43(9):1158-62 (2004).
Mackman et al., "Role of the Extrinsic Pathway of Blood Coagulation in Hemostasis and Thrombosis," Arterisocler Thromb Vasc Biol, 27: 1687-1693 (2007).
Mitchell et al., "Polyarginine enters cells more efficiently than oter polycationic homopolymers," J Peptide Res, 56:318-25 (2000).
Mosmann, "Rapid colorimetric assay for cellular growth and survival: Application to proliferation and cytotoxicity assays," J Immunol Meth, 65:55-63 (1983).
Murriel et al., "Influence of protein transduction on intracellular delivery of macromolecules," Expert Opin Drug Deliv, 3(6):739-46 (2006).
Nowak et al., "Rapidly recovering hydrogels scaffolds from self-assembling diblock copolypeptide amphiphiles," Nature, 417(6887):424-8 (2002).
Oie et al., "Microbial contamination of antiseptics and disinfectants," Am J Infect Control, 24(5):389-95 (1996).
Pakstis et al., "Effect of chemistry and morphology on the biofunctionality of self-assembling diblock copolypeptide hydrogels," Biomacromol, 5:312-8 (2004).
Pandey et al., "Glycopolypeptide-Grafted Bioactive Polyionic Complex Vesicles (PICsomes) and Their Specific Polyvalent Interactions," ACS Omega, 1(4):600-612 (2016).
Picout et al., "Rheology of biopolymer solutions and gels," The Scientific World Journal, 3:105-21 (2003).
Porter et al., "Mimicry of host-defense peptides by unnatural oligomers: Antimicrobial beta-peptides," J Am Chem Soc, 124(25):7324-30 (2002).

(56) References Cited

OTHER PUBLICATIONS

Proctor, "Blood substitutes and experimental models of trauma," J Trauma, 54:S106 (2003).
Rabinovici et al., "Liposome-encapsulated hemoglobin: an oxygen-carrying fluid," Circulatory Shock, 32:1 (1990).
Riess, "Oxygen carriers ("blood substitutes")—raison d'etre, chemistry, and some physiology," Chem Rev 101(9):2797-920 (2001).
Rodriguez et al., "Enzyme-triggered cargo release from methionine sulfoxide containing copolypeptide vesicles," Biomacromolecules, 14(10):3610-3614 (2013).
Rothbard et al., "Adaptive translocation: The role of hydrogen bonding and membrane potential in the uptake of guanidinium-rich transporters into cells," Adv Drug Deliv Rev, 57:495-504 (2005).
Rothbard et al., "Conjugation of arginine oligomers to cyclosporin A facilitates topical delivery and inhibition of inflammation," Nat Med, 6:1253-7 (2000).
Rothbard et al., "Role of membrane potential hydrogen bonding in the mechanism of translocation of guanidinium-rich peptides into cells," J Am Chem Soc, 126:9506-7 (2004).
Sakai et al., "Anion-mediated transfer of polyarginine across liquid and bilayer membranes," J Am Chem Soc, 125:14348-56 (2003).
Salick et al., "Inherent antibacterial activity of a peptide-based beta-hairpin hydrogel," J Am Chem Soc, 129(47):14793-9 (2007).
Sela et al., "Biological properties of poly amino acids," Adv Protein Chem, 14:391-478 (1959).
SG 201310360-2 Examination Report dated Jun. 24, 2014.
Song et al., "Sustained local delivery of bioactive nerve growth factor in the central nervous system via tunable diblock copolypeptide hydrogel depots," Biomater, 33:9105-16 (2012).
Stickler et al., "Antiseptic and antibiotic resistance in gram-negative bacteria causing urinary tract infection," J Clin Pathol, 33(3):288-96 (1980).
Sun et al., "Conformation-Directed Formation of Self-Healing Diblock Copolypeptide Hydrogels via Polyion Complexation," Journal of the American Chemical Society, 139(42):15114-15121 (2017).
Supplementary European Search Report dated Nov. 9, 2012.
Tew et al., "Antimicrobial activity of an abiotic host defense peptide mimic," Biochim Biophys Acta, 1758(9):1387-92 (2006).
Tian et al., "Hyaluronic acid-poly-D-lysine-based three-dimensional hydrogel for traumatic brain injury," Tissue Eng, 11(3-4):513-25 (2005).
Tjong et al., "Prediction of Protein Solubility from Calculation of Transfer Free Energy," Biophys J, 95(6): 2601-2609 (2008).
Torchilin et al., "TAT peptide on the surface of liposomes affords their efficient intracellular delivery even at low temperature and in the presence of metabolic inhibitors," Proc Natl Acad Sci USA, 98:9786-91 (2001).
Tseng et al., "Translocation of liposomes into cancer cells by cell-penetrating peptides Peenetratin and Tat: A kinetic and efficacy study," Mol Pharmacol, 62:864-72 (2002).
Wadia et al., "Transducible TAT-HA fusogenic peptide enhances escape of TAT-fusion proteins after lipid raft macropinocytosis," Nat Med, 10:310-5 (2004).
Wadia et al., "Transmembrane delivery of protein and peptide drugs by TAT-mediated transduction in the treatment of cancer," Adv Drug Deliv Rev, 57:579-596 (2005).
Wang et al., "Antimicrobial and hemolytic activities of copolymers with cationic and hydrophobic groups: A comparison of block and random copolymers," Macromol Biosci, 11(11):1499-504 (2011).
Wyrsta et al., "A parallel synthetic approach for the analysis of membrane interactive copolypeptides," J Am Chem Soc, 123(51):12919-20 (2001).
Wyrsta et al., "Synthesis and Studies of Polypeptide Materials: Self-assembled Block Copolypepetide Amphiphiles, DNA-condensing Block Copolypeptides and Membrane-interactive Random Copolypeptides," University of California, Santa Barbara, p. 125 (2002).
Yang et al., "Biocompatibility of amphiphilic diblock copolypeptide hydrogels in the central nervous system," Biomaterials, 30(15):2881-98 (2009).
Yeaman et al., "Mechanisms of antimicrobial peptide action and resistance," Pharmacol Rev, 55(1):27-55 (2003).
Zaiou et al., "Multifunctional antimicrobial peptides: Therapeutic targets in several human diseases," J Mol Med (Berl), 85(4):317-29 (2007).
Zasloff et al., "Antimicrobial peptides of multicellular organisms," Nature, 415(6870):389-95 (2002).
Zhang et al., "Design and synthesis of nonionic copolypeptide hydrogels with reversible thermoresponsive and tunable physical properties," Biomacromol, 16:1331-40 (2015).
Zhang et al., "Supramolecular hydrogels assembled from nonionic poly (ethylene glycol)-b-polypeptide diblocks containing oegylated poly-L-glutamate," Polym Chem, 5:3346-51 [e-pub] (2014).
Zhang et al., "Thermoresponsive copolypeptide hydrogel vehicles for central nervous system cell delivery," ACS Biomater Sci Eng, 1:705-17 (2015).
Zhang et al., "Tunable diblock copolypeptide hydrogel depots for local delivery of hydrophobic molecules in healthy and injured central nervous system," Biomater, 35:1989-2000 (2014).
Zhou et al., "High potency and broad-spectrum antimicrobial peptides synthesized via ring-opening polymerization of alpha-aminoacid-N-carboxyanhydrides," Biomacromolecules, 11(1):60-7 (2010).
Bashir et al., "Fundamental concepts of hydrogels: Synthesis, properties, and their applications." Polymers 12(2020): 2702.
Fan et al., "Fabrication of bioinspired hydrogels: challenges and opportunities." Macromolecules 53 (2020): 2769-2782.
Ho et al., "Hydrogels: Properties and applications in biomedicine." *Molecules* 27 (2022): 2902.
Ozer et al., "The Usage of PEG in Drug Delivery Systems—A Mini Review," Polymer Science: Peer Review Journal 3.4 (2022): 000566 (4 pages).
Xu et al., "Structures of single-layer B-sheet proteins evolved from β-hairpin repeats." Protein Science 28 (2019): 1676-1689.

\* cited by examiner

SEQUENCE LISTING

<160> NUMBER OF SEQ ID NOS: 33

<210> SEQ ID NO 1
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala

<400> SEQUENCE: 1

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Lys Lys Lys Lys Lys
145                 150                 155                 160

Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys Lys
        195                 200                 205

Lys Lys Lys Lys Lys Lys Lys
    210                 215

<210> SEQ ID NO 2
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala

<400> SEQUENCE: 2

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

```
Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Glu Glu Glu Glu Glu
145                 150                 155                 160

Glu Glu Glu Glu Glu Glu Glu Glu Glu Glu Glu Glu Glu Glu Glu
            165                 170                 175

Glu Glu Glu Glu Glu Glu Glu Glu Glu Glu Glu Glu Glu Glu Glu
            180                 185                 190

Glu Glu Glu Glu Glu Glu Glu Glu Glu Glu Glu Glu Glu Glu Glu
            195                 200                 205

Glu Glu Glu Glu Glu Glu Glu
            210                 215

<210> SEQ ID NO 3
<211> LENGTH: 200
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 3

Lys Lys Lys Lys Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys Lys
             20                  25                  30

Lys Lys Lys Lys Lys Lys Lys Lys Lys Lys Lys Lys Lys Lys Lys
             35                  40                  45

Lys Lys Lys Lys Lys Lys Lys Lys Lys Lys Lys Lys Lys Lys Lys
         50                  55                  60

Lys Lys Lys Lys Lys Lys Lys Lys Lys Lys Lys Lys Lys Lys Lys Lys
 65                  70                  75                  80

Lys Lys Lys Lys Lys Lys Lys Lys Lys Lys Lys Lys Lys Lys Lys
             85                  90                  95

Lys Lys Lys Lys Lys Lys Lys Lys Lys Lys Lys Lys Lys Lys Lys
            100                 105                 110

Lys Lys Lys Lys Lys Lys Lys Lys Lys Lys Lys Lys Lys Lys Lys
            115                 120                 125

Lys Lys Lys Lys Lys Lys Lys Lys Lys Lys Lys Lys Lys Lys Lys
            130                 135                 140

Lys Lys Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys Lys
            165                 170                 175

Lys Lys Lys Lys Leu Leu Leu Leu Leu Leu Leu Leu Leu Leu Leu
            180                 185                 190

Leu Leu Leu Leu Leu Leu Leu Leu
            195                 200
```

<210> SEQ ID NO 4
<211> LENGTH: 275
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Met or Ala
<220> FEATURE:
<221> NAME/KEY: MOD_RES
<222> LOCATION: (156)..(275)
<223> OTHER INFORMATION: Epsilon-trifluoroacetyl-L-lysine

<400> SEQUENCE: 4

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Lys Lys Lys Lys Lys
145                 150                 155                 160

Lys Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys Lys Lys
        195                 200                 205

Lys Lys Lys Lys Lys Lys Lys Lys Lys Lys Lys Lys Lys Lys Lys Lys
    210                 215                 220

Lys Lys Lys Lys Lys Lys Lys Lys Lys Lys Lys Lys Lys Lys Lys Lys
225                 230                 235                 240

Lys Lys Lys Lys Lys Lys Lys Lys Lys Lys Lys Lys Lys Lys Lys Lys
                245                 250                 255

Lys Lys Lys Lys Lys Lys Lys Lys Lys Lys Lys Lys Lys Lys Lys Lys
            260                 265                 270

Lys Lys Lys
        275

<210> SEQ ID NO 5
<211> LENGTH: 275
<212> TYPE: PRT
<213> ORGANISM: Artificial Sequence -continued

```
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Met or Ala
<220> FEATURE:
<221> NAME/KEY: MOD_RES
<222> LOCATION: (156)..(275)
<223> OTHER INFORMATION: Gamma-benzyl-L-glutamate

<400> SEQUENCE: 5

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Glu Glu Glu Glu Glu Glu
145                 150                 155                 160

Glu Glu Glu Glu Glu Glu Glu Glu Glu Glu Glu Glu Glu Glu Glu Glu
                165                 170                 175

Glu Glu Glu Glu Glu Glu Glu Glu Glu Glu Glu Glu Glu Glu Glu Glu
            180                 185                 190

Glu Glu Glu Glu Glu Glu Glu Glu Glu Glu Glu Glu Glu Glu Glu Glu
        195                 200                 205

Glu Glu Glu Glu Glu Glu Glu Glu Glu Glu Glu Glu Glu Glu Glu Glu
210                 215                 220

Glu Glu Glu Glu Glu Glu Glu Glu Glu Glu Glu Glu Glu Glu Glu Glu
225                 230                 235                 240

Glu Glu Glu Glu Glu Glu Glu Glu Glu Glu Glu Glu Glu Glu Glu Glu
                245                 250                 255

Glu Glu Glu Glu Glu Glu Glu Glu Glu Glu Glu Glu Glu Glu Glu Glu
            260                 265                 270

Glu Glu Glu
        275

<210> SEQ ID NO 6
<211> LENGTH: 105
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(105)
```

<223> OTHER INFORMATION: Methionine sulfoxide

<400> SEQUENCE: 6

```
Met Met Met Met Met Met Met Met Met Met Met Met Met Met Met
1               5                   10                  15

Met Met Met Met Met Met Met Met Met Met Met Met Met Met Met
            20                  25                  30

Met Met Met Met Met Met Met Met Met Met Met Met Met Met Met
        35                  40                  45

Met Met Met Met Met Met Met Met Met Met Met Met Met Met Met
    50                  55                  60

Met Met Met Met Met Met Met Met Met Met Met Met Met Met Met
65                  70                  75                  80

Met Met Met Met Met Met Met Met Met Met Met Met Met Met Met
            85                  90                  95

Met Met Met Met Met Met Met Met Met
            100                 105
```

<210> SEQ ID NO 7
<211> LENGTH: 185
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala

<400> SEQUENCE: 7

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Lys Lys Lys Lys Lys
145                 150                 155                 160

Lys Lys Lys Lys Lys Lys Lys Lys Lys Lys Lys Lys Lys Lys Lys
            165                 170                 175

Lys Lys Lys Lys Lys Lys Lys Lys Lys
            180                 185
```

<210> SEQ ID NO 8
<211> LENGTH: 245

```
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala

<400> SEQUENCE: 8

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Glu Glu Glu Glu Glu
145                 150                 155                 160

Glu Glu Glu Glu Glu Glu Glu Glu Glu Glu Glu Glu Glu Glu Glu
                165                 170                 175

Glu Glu Glu Glu Glu Glu Glu Glu Glu Glu Glu Glu Glu Glu Glu
            180                 185                 190

Glu Glu Glu Glu Glu Glu Glu Glu Glu Glu Glu Glu Glu Glu Glu
        195                 200                 205

Glu Glu Glu Glu Glu Glu Glu Glu Glu Glu Glu Glu Glu Glu Glu
    210                 215                 220

Glu Glu Glu Glu Glu Glu Glu Glu Glu Glu Glu Glu Glu Glu Glu
225                 230                 235                 240

Glu Glu Glu Glu Glu
                245

<210> SEQ ID NO 9
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala
<220> FEATURE:
<221> NAME/KEY: MOD_RES
<222> LOCATION: (156)..(215)
<223> OTHER INFORMATION: Racemic Glu

<400> SEQUENCE: 9
```

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Glu Glu Glu Glu Glu
145                 150                 155                 160

Glu Glu Glu Glu Glu Glu Glu Glu Glu Glu Glu Glu Glu Glu Glu
                165                 170                 175

Glu Glu Glu Glu Glu Glu Glu Glu Glu Glu Glu Glu Glu Glu Glu
            180                 185                 190

Glu Glu Glu Glu Glu Glu Glu Glu Glu Glu Glu Glu Glu Glu Glu
        195                 200                 205

Glu Glu Glu Glu Glu Glu Glu
    210                 215

<210> SEQ ID NO 10
<211> LENGTH: 185
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala

<400> SEQUENCE: 10

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa

```
                  115                 120                 125

Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Glu Glu Glu Glu Glu
145                 150                 155                 160

Glu Glu Glu Glu Glu Glu Glu Glu Glu Glu Glu Glu Glu Glu
                165                 170                 175

Glu Glu Glu Glu Glu Glu Glu Glu Glu
        180                 185

<210> SEQ ID NO 11
<211> LENGTH: 275
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala

<400> SEQUENCE: 11

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Glu Glu Glu Glu Glu
145                 150                 155                 160

Glu Glu Glu Glu Glu Glu Glu Glu Glu Glu Glu Glu Glu Glu Glu
                165                 170                 175

Glu Glu Glu Glu Glu Glu Glu Glu Glu Glu Glu Glu Glu Glu Glu
            180                 185                 190

Glu Glu Glu Glu Glu Glu Glu Glu Glu Glu Glu Glu Glu Glu Glu
        195                 200                 205

Glu Glu Glu Glu Glu Glu Glu Glu Glu Glu Glu Glu Glu Glu Glu
    210                 215                 220

Glu Glu Glu Glu Glu Glu Glu Glu Glu Glu Glu Glu Glu Glu Glu
225                 230                 235                 240

Glu Glu Glu Glu Glu Glu Glu Glu Glu Glu Glu Glu Glu Glu Glu
                245                 250                 255

Glu Glu Glu Glu Glu Glu Glu Glu Glu Glu Glu Glu Glu Glu Glu
            260                 265                 270
```

Glu Glu Glu
       275

<210> SEQ ID NO 12
<211> LENGTH: 245
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala

<400> SEQUENCE: 12

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Lys Lys Lys Lys Lys Lys
145                 150                 155                 160

Lys Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys Lys Lys
        195                 200                 205

Lys Lys Lys Lys Lys Lys Lys Lys Lys Lys Lys Lys Lys Lys Lys Lys
    210                 215                 220

Lys Lys Lys Lys Lys Lys Lys Lys Lys Lys Lys Lys Lys Lys Lys Lys
225                 230                 235                 240

Lys Lys Lys Lys Lys
            245

<210> SEQ ID NO 13
<211> LENGTH: 275
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala

<400> SEQUENCE: 13

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Lys Lys Lys Lys Lys
145                 150                 155                 160

Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys Lys
        195                 200                 205

Lys Lys Lys Lys Lys Lys Lys Lys Lys Lys Lys Lys Lys Lys Lys
    210                 215                 220

Lys Lys Lys Lys Lys Lys Lys Lys Lys Lys Lys Lys Lys Lys Lys
225                 230                 235                 240

Lys Lys Lys Lys Lys Lys Lys Lys Lys Lys Lys Lys Lys Lys Lys
                245                 250                 255

Lys Lys Lys Lys Lys Lys Lys Lys Lys Lys Lys Lys Lys Lys Lys
            260                 265                 270

Lys Lys Lys
        275

<210> SEQ ID NO 14
<211> LENGTH: 183
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(156)
<223> OTHER INFORMATION: Methionine sulfoxide or Ala

<400> SEQUENCE: 14

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa

```
                35                  40                  45
Xaa Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Glu Glu Glu Glu
145                 150                 155                 160

Glu Glu Glu Glu Glu Glu Glu Glu Glu Glu Glu Glu Glu Glu Glu
                165                 170                 175

Glu Glu Glu Glu Glu Glu Glu
            180

<210> SEQ ID NO 15
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(156)
<223> OTHER INFORMATION: Methionine sulfoxide or Ala

<400> SEQUENCE: 15

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Glu Glu Glu Glu
145                 150                 155                 160

Glu Glu Glu Glu Glu Glu Glu Glu Glu Glu Glu Glu Glu Glu Glu
                165                 170                 175

Glu Glu Glu Glu Glu Glu Glu Glu Glu Glu Glu Glu Glu Glu Glu
            180                 185                 190
```

Glu Glu Glu Glu Glu Glu Glu Glu Glu Glu Glu Glu Glu Glu
        195                 200                 205

Glu Glu Glu Glu Glu Glu Glu
    210                 215

<210> SEQ ID NO 16
<211> LENGTH: 244
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(156)
<223> OTHER INFORMATION: Methionine sulfoxide or Ala

<400> SEQUENCE: 16

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Glu Glu Glu Glu
145                 150                 155                 160

Glu Glu Glu Glu Glu Glu Glu Glu Glu Glu Glu Glu Glu Glu
            165                 170                 175

Glu Glu Glu Glu Glu Glu Glu Glu Glu Glu Glu Glu Glu Glu
        180                 185                 190

Glu Glu Glu Glu Glu Glu Glu Glu Glu Glu Glu Glu Glu Glu
    195                 200                 205

Glu Glu Glu Glu Glu Glu Glu Glu Glu Glu Glu Glu Glu Glu
210                 215                 220

Glu Glu Glu Glu Glu Glu Glu Glu Glu Glu Glu Glu Glu Glu Glu Glu
225                 230                 235                 240

Glu Glu Glu Glu

<210> SEQ ID NO 17
<211> LENGTH: 273
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(156)
<223> OTHER INFORMATION: Methionine sulfoxide or Ala

<400> SEQUENCE: 17

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Glu Glu Glu Glu
145                 150                 155                 160

Glu Glu Glu Glu Glu Glu Glu Glu Glu Glu Glu Glu Glu Glu Glu
                165                 170                 175

Glu Glu Glu Glu Glu Glu Glu Glu Glu Glu Glu Glu Glu Glu Glu
            180                 185                 190

Glu Glu Glu Glu Glu Glu Glu Glu Glu Glu Glu Glu Glu Glu Glu
        195                 200                 205

Glu Glu Glu Glu Glu Glu Glu Glu Glu Glu Glu Glu Glu Glu Glu
    210                 215                 220

Glu Glu Glu Glu Glu Glu Glu Glu Glu Glu Glu Glu Glu Glu Glu
225                 230                 235                 240

Glu Glu Glu Glu Glu Glu Glu Glu Glu Glu Glu Glu Glu Glu Glu
                245                 250                 255

Glu Glu Glu Glu Glu Glu Glu Glu Glu Glu Glu Glu Glu Glu Glu
            260                 265                 270

Glu

<210> SEQ ID NO 18
<211> LENGTH: 212
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(156)
<223> OTHER INFORMATION: Methionine sulfoxide or Ala
<220> FEATURE:
<221> NAME/KEY: MOD_RES
<222> LOCATION: (157)..(212)
<223> OTHER INFORMATION: Racemic Glu

<400> SEQUENCE: 18

Xaa Xaa Xaa Xaa Xaa Xaa Xaa Xaa Xaa Xaa Xaa Xaa Xaa Xaa Xaa
1               5                   10                  15

```
Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
50                      55                  60

Xaa Xaa Xaa Xaa Xaa Xaa Xaa Xaa Xaa Xaa Xaa Xaa Xaa Xaa Xaa
65                      70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Glu Glu Glu Glu
145                     150                 155                 160

Glu Glu Glu Glu Glu Glu Glu Glu Glu Glu Glu Glu Glu Glu Glu
            165                 170                 175

Glu Glu Glu Glu Glu Glu Glu Glu Glu Glu Glu Glu Glu Glu Glu
            180                 185                 190

Glu Glu Glu Glu Glu Glu Glu Glu Glu Glu Glu Glu Glu Glu Glu
            195                 200                 205

Glu Glu Glu Glu
        210

<210> SEQ ID NO 19
<211> LENGTH: 184
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(156)
<223> OTHER INFORMATION: Methionine sulfoxide or Ala

<400> SEQUENCE: 19

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
50                      55                  60

Xaa Xaa Xaa Xaa Xaa Xaa Xaa Xaa Xaa Xaa Xaa Xaa Xaa Xaa Xaa
65                      70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125
```

Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Lys Lys Lys Lys
145                 150                 155                 160

Lys Lys Lys Lys Lys Lys Lys Lys Lys Lys Lys Lys Lys Lys
            165                 170                 175

Lys Lys Lys Lys Lys Lys Lys Lys
        180

<210> SEQ ID NO 20
<211> LENGTH: 218
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(156)
<223> OTHER INFORMATION: Methionine sulfoxide or Ala

<400> SEQUENCE: 20

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Lys Lys Lys Lys
145                 150                 155                 160

Lys Lys Lys Lys Lys Lys Lys Lys Lys Lys Lys Lys Lys Lys
            165                 170                 175

Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys
        195                 200                 205

Lys Lys Lys Lys Lys Lys Lys Lys Lys
    210                 215

<210> SEQ ID NO 21
<211> LENGTH: 244
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(156)
<223> OTHER INFORMATION: Methionine sulfoxide or Ala

<400> SEQUENCE: 21

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Lys Lys Lys Lys
145                 150                 155                 160

Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys Lys
        195                 200                 205

Lys Lys Lys Lys Lys Lys Lys Lys Lys Lys Lys Lys Lys Lys Lys
    210                 215                 220

Lys Lys Lys Lys Lys Lys Lys Lys Lys Lys Lys Lys Lys Lys Lys
225                 230                 235                 240

Lys Lys Lys Lys

<210> SEQ ID NO 22
<211> LENGTH: 275
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(156)
<223> OTHER INFORMATION: Methionine sulfoxide or Ala

<400> SEQUENCE: 22

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

```
Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Lys Lys Lys Lys Lys
145                 150                 155                 160

Lys Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys Lys Lys
        195                 200                 205

Lys Lys Lys Lys Lys Lys Lys Lys Lys Lys Lys Lys Lys Lys Lys Lys
    210                 215                 220

Lys Lys Lys Lys Lys Lys Lys Lys Lys Lys Lys Lys Lys Lys Lys Lys
225                 230                 235                 240

Lys Lys Lys Lys Lys Lys Lys Lys Lys Lys Lys Lys Lys Lys Lys Lys
                245                 250                 255

Lys Lys Lys Lys Lys Lys Lys Lys Lys Lys Lys Lys Lys Lys Lys Lys
            260                 265                 270

Lys Lys Lys
        275

<210> SEQ ID NO 23
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Met or Ala
<220> FEATURE:
<221> NAME/KEY: MOD_RES
<222> LOCATION: (156)..(215)
<223> OTHER INFORMATION: Epsilon-trifluoroacetyl-L-lysine

<400> SEQUENCE: 23

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95
```

Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Lys Lys Lys Lys Lys
145                 150                 155                 160

Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys Lys
        195                 200                 205

Lys Lys Lys Lys Lys Lys Lys
    210                 215

<210> SEQ ID NO 24
<211> LENGTH: 210
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Met or Ala
<220> FEATURE:
<221> NAME/KEY: MOD_RES
<222> LOCATION: (156)..(210)
<223> OTHER INFORMATION: Epsilon-trifluoroacetyl-L-lysine

<400> SEQUENCE: 24

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Lys Lys Lys Lys Lys
145                 150                 155                 160

Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys
            195                 200                 205

Lys Lys
    210

<210> SEQ ID NO 25
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Met or Ala
<220> FEATURE:
<221> NAME/KEY: MOD_RES
<222> LOCATION: (156)..(215)
<223> OTHER INFORMATION: Gamma-benzyl-L-glutamate

<400> SEQUENCE: 25

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Glu Glu Glu Glu
145                 150                 155                 160

Glu Glu Glu Glu Glu Glu Glu Glu Glu Glu Glu Glu Glu Glu Glu
                165                 170                 175

Glu Glu Glu Glu Glu Glu Glu Glu Glu Glu Glu Glu Glu Glu Glu
            180                 185                 190

Glu Glu Glu Glu Glu Glu Glu Glu Glu Glu Glu Glu Glu Glu Glu
        195                 200                 205

Glu Glu Glu Glu Glu Glu Glu
    210                 215

<210> SEQ ID NO 26
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Met or Ala

```
<220> FEATURE:
<221> NAME/KEY: MOD_RES
<222> LOCATION: (156)..(215)
<223> OTHER INFORMATION: Gamma-benzyl-L-glutamate

<400> SEQUENCE: 26

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Glu Glu Glu Glu Glu
145                 150                 155                 160

Glu Glu Glu Glu Glu Glu Glu Glu Glu Glu Glu Glu Glu Glu Glu
                165                 170                 175

Glu Glu Glu Glu Glu Glu Glu Glu Glu Glu Glu Glu Glu Glu Glu
            180                 185                 190

Glu Glu Glu Glu Glu Glu Glu Glu Glu Glu Glu Glu Glu Glu Glu
        195                 200                 205

Glu Glu Glu Glu Glu Glu Glu
    210                 215

<210> SEQ ID NO 27
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Met or Ala
<220> FEATURE:
<221> NAME/KEY: MOD_RES
<222> LOCATION: (156)..(215)
<223> OTHER INFORMATION: Epsilon-trifluoroacetyl-L-lysine

<400> SEQUENCE: 27

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60
```

```
Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Lys Lys Lys Lys Lys
145                 150                 155                 160

Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys Lys
        195                 200                 205

Lys Lys Lys Lys Lys Lys Lys
    210                 215

<210> SEQ ID NO 28
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala
<220> FEATURE:
<221> NAME/KEY: MOD_RES
<222> LOCATION: (156)..(215)
<223> OTHER INFORMATION: Epsilon-trifluoroacetyl-L-lysine

<400> SEQUENCE: 28

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Lys Lys Lys Lys Lys
145                 150                 155                 160
```

Lys Lys Lys Lys Lys Lys Lys Lys Lys Lys Lys Lys Lys Lys
            165                 170                 175

Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys
            195                 200                 205

Lys Lys Lys Lys Lys Lys Lys
    210                 215

<210> SEQ ID NO 29
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala
<220> FEATURE:
<221> NAME/KEY: MOD_RES
<222> LOCATION: (156)..(215)
<223> OTHER INFORMATION: Epsilon-trifluoroacetyl-L-lysine

<400> SEQUENCE: 29

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Lys Lys Lys Lys Lys
145                 150                 155                 160

Lys Lys Lys Lys Lys Lys Lys Lys Lys Lys Lys Lys Lys Lys
            165                 170                 175

Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys
            195                 200                 205

Lys Lys Lys Lys Lys Lys Lys
    210                 215

<210> SEQ ID NO 30
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala
<220> FEATURE:
<221> NAME/KEY: MOD_RES
<222> LOCATION: (156)..(215)
<223> OTHER INFORMATION: Gamma-benzyl-L-glutamate

<400> SEQUENCE: 30

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Glu Glu Glu Glu
145                 150                 155                 160

Glu Glu Glu Glu Glu Glu Glu Glu Glu Glu Glu Glu Glu Glu Glu
                165                 170                 175

Glu Glu Glu Glu Glu Glu Glu Glu Glu Glu Glu Glu Glu Glu Glu
            180                 185                 190

Glu Glu Glu Glu Glu Glu Glu Glu Glu Glu Glu Glu Glu Glu Glu
        195                 200                 205

Glu Glu Glu Glu Glu Glu Glu
    210                 215

<210> SEQ ID NO 31
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala
<220> FEATURE:
<221> NAME/KEY: MOD_RES
<222> LOCATION: (156)..(275)
<223> OTHER INFORMATION: Gamma-benzyl-L-glutamate

<400> SEQUENCE: 31

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa

```
                    20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Glu Glu Glu Glu Glu
145                 150                 155                 160

Glu Glu Glu Glu Glu Glu Glu Glu Glu Glu Glu Glu Glu Glu Glu
                165                 170                 175

Glu Glu Glu Glu Glu Glu Glu Glu Glu Glu Glu Glu Glu Glu Glu
            180                 185                 190

Glu Glu Glu Glu Glu Glu Glu Glu Glu Glu Glu Glu Glu Glu Glu
    195                 200                 205

Glu Glu Glu Glu Glu Glu Glu
        210                 215

<210> SEQ ID NO 32
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala

<400> SEQUENCE: 32

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140
```

```
Xaa Xaa Xaa Xaa Xaa Xaa Xaa Xaa Xaa Xaa Lys Lys Lys Lys
145                 150                 155             160

Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys
        195                 200                 205

Lys Lys Lys Lys Lys Lys Lys
    210                 215

<210> SEQ ID NO 33
<211> LENGTH: 215
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(155)
<223> OTHER INFORMATION: Methionine sulfoxide or Ala

<400> SEQUENCE: 33

Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Glu Glu Glu Glu
145                 150                 155             160

Glu Glu Glu Glu Glu Glu Glu Glu Glu Glu Glu Glu Glu Glu
                165                 170                 175

Glu Glu Glu Glu Glu Glu Glu Glu Glu Glu Glu Glu Glu Glu
            180                 185                 190

Glu Glu Glu Glu Glu Glu Glu Glu Glu Glu Glu Glu Glu Glu
        195                 200                 205

Glu Glu Glu Glu Glu Glu Glu
    210                 215
```

POLYION COMPLEX POLYPEPTIDE HYDROGELS AND USES THEREOF

RELATED APPLICATIONS

This application is the U.S. national phase of International Patent Application No. PCT/US18/53050, filed on Sep. 27, 2018, which claims the benefit of U.S. Provisional Patent Application No. 62/564,765, filed on Sep. 28, 2017. The contents of each application are hereby incorporated by reference in their entirety.

REFERENCE TO A SEQUENCE LISTING

This application contains a Sequence Listing in computer readable form. The computer readable form is incorporated herein by reference. Said ASCII copy, created on Jun. 20, 2022 is named UCH-13101_SL.txt and is 71,166 bytes in size.

BACKGROUND

Polypeptide containing block copolymer assemblies, such as micelles, vesicles, and hydrogels, have been prepared using polyion complexes (PICs), where oppositely charged chain segments aggregate and phase separate upon mixing in aqueous media. In these systems, as well as those based on other synthetic polymers, formation of unstructured, liquid PIC coacervate domains is common and often desired. Fluidity in PIC coacervates can assist rapid complex formation and equilibration, while formation of solid β-sheet structures can lead to irregular assemblies with less desirable properties.

Most polypeptide containing PIC assemblies utilize polyethylene glycol (PEG) chains as hydrophilic non-ionic segments, as well as ionic polypeptide segments that form disordered or liquid coacervate immiscible phases. The resulting lack of internal order in the complexes tends to favor formation of spherical assemblies as found in diblock copolymer micelles and triblock copolymer hydrogels. In the few examples where internal order has been incorporated into polypeptide PIC assemblies, via use of ionic α-helical segments or by β-sheet formation during assembly, only minimal perturbation of spherical micelle formation or slowed formation of micelles with increased polydispersity was observed. While there are examples of peptides and polypeptides where β-sheet structures are used to direct formation of self-assembled materials, these all rely on other components, such as hydrophobic and non-ionic residues to drive β-sheet formation.

SUMMARY

In certain embodiments, the invention relates to a composition comprising a first copolypeptide comprising Substructure I, a second copolypeptide comprising Substructure II, and water, wherein Substructure I is depicted as follows:

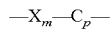  Substructure I;

Substructure II is depicted as follows:

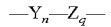  Substructure II;

each instance of X is an amino acid residue independently selected from a non-ionic, hydrophilic amino acid, glycine, and alanine;

each instance of Y is an amino acid residue independently selected from a non-ionic, hydrophilic amino acid, glycine, and alanine;

each instance of C is an amino acid residue independently selected from a cationic, hydrophilic amino acid;

each instance of Z is an amino acid residue independently selected from an anionic, hydrophilic amino acid;

m is about 100 to about 600;

n is about 100 to about 600;

p is about 20 to about 200;

q is about 20 to about 200;

at least 90 mol % of the C amino acid residues are (D)-amino acid residues or at least 90 mol % of the C amino acid residues are (L)-amino acid residues; and at least 90 mol % of the Z amino acid residues are (D)-amino acid residues or at least 90 mol % of the Z amino acid residues are (L)-amino acid residues.

DESCRIPTION

Overview

In certain embodiments, the invention relates to compositions comprising synthetic diblock copolypeptides having oppositely charged ionic segments, which form β-sheet structured hydrogel assemblies via polyion complexation when mixed in aqueous media. In certain embodiments, the hydrogels of the invention are self-healing after deformation, exhibit rapid recovery after stress, are microporous, or are stable against dilution in aqueous media. In certain embodiments, the compositions are useful as cell suspension or cell culture media, in drug or cell delivery systems, in scaffolds for tissue repair, or as 3D-printable media.

In certain embodiments, the diblock copolypeptide hydrogels ($DCH_{PIC}$) assemble via ordered chain conformations, which is different from other PIC hydrogels that require triblock copolymers and utilize disordered conformations.

In certain embodiments, the $DCH_{PIC}$ possess certain advantages over hydrophobically assembled DCH in that they are resistant to dilution in aqueous media, and are readily prepared at high concentrations for increased hydrogel stiffness.

In certain embodiments, the invention relates to a composition comprising a first copolypeptide, a second copolypeptide, and water, wherein the first copolypeptide comprises a first segment consisting essentially of lysine residues, and the second copolypeptide comprises a first segment consisting essentially of glutamic acid residues. In certain embodiments, greater than 90% of the lysine residues are (L)-lysine. In certain embodiments, the lysine residues are all (L)-lysine. In certain embodiments, greater than 90% of the lysine residues are (D)-lysine. In certain embodiments, the lysine residues are all (D)-lysine. In certain embodiments, greater than 90% of the glutamic acid residues are (L)-glutamic acid. In certain embodiments, the glutamic acid residues are all (L)-glutamic acid. In certain embodiments, greater than 90% of the glutamic acid residues are (D)-glutamic acid. In certain embodiments, the glutamic acid residues are all (D)-glutamic acid.

In certain embodiments, neither the first copolypeptide nor the second copolypeptide comprises a repeat unit that is not derived from an amino acid.

In certain embodiments, the first copolypeptide comprises a second segment, wherein the second segment is non-ionic. In certain embodiments, the second copolypeptide comprises a second segment, wherein the second segment is non-ionic. In certain embodiments, the second segment is disordered. In certain embodiments, the second segment is hydrophilic. In certain embodiments, the second segment comprises a plurality of L-methionine sulfoxide, $M^O$, residues. Poly(L-methionine sulfoxide) is readily prepared, avoids the need to use racemic amino acid monomers, and is a naturally occurring residue that shows minimal toxicity.

Figure 1:
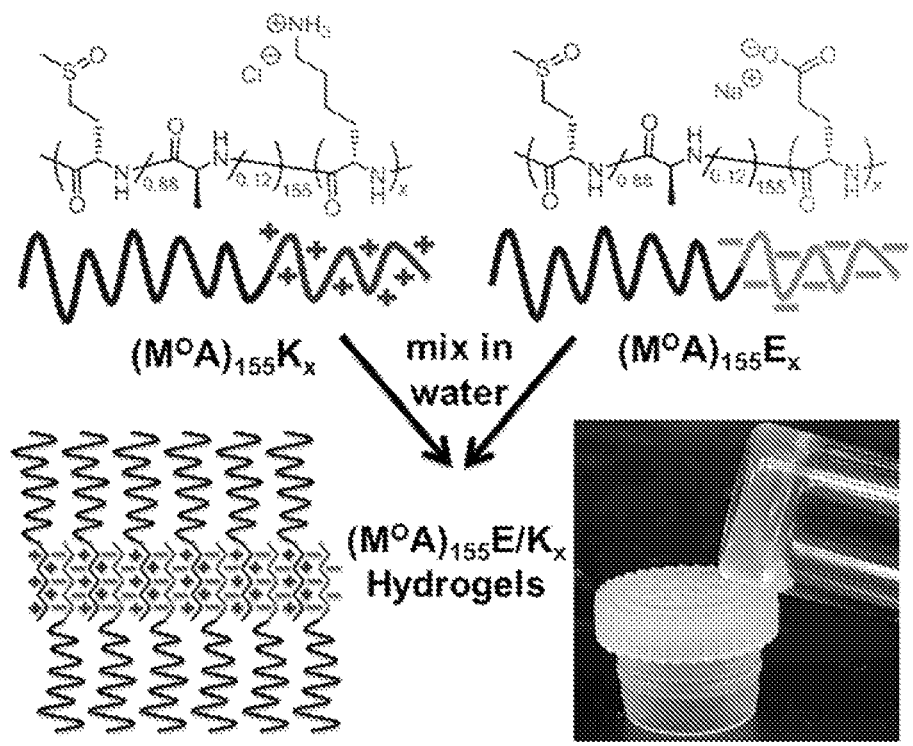
FIG. 1 depicts a schematic representation of the assembly process for preparation of polyion complex $(M^OA)_{155}E/K_x$ diblock copolypeptide hydrogels.

In certain embodiments, the $DCH_{PIC}$ compositions comprise long, disordered hydrophilic segments as well as oppositely charged ionic segments able to form β-sheet complexes upon mixing (e.g., FIG. 1). For shorter hydrophilic segment lengths (ca. 60 residues), non-ionic, hydrophilic $M^O$ segments may be prepared from poly(L-methionine), M, precursors by post-polymerization oxidation. At longer hydrophilic segment lengths, e.g. >100 residues, L-alanine N-carboxyanhydride (NCA) monomer (ca. 12 mol %) may be mixed with L-methionine NCA to prepare statistical copolymer segments that do not aggregate during polymerization. The incorporation of a small amount of minimally hydrophobic alanine was found to allow efficient copolypeptide synthesis without adversely affecting the water solubility or disordered conformation of the resulting poly(L-methionine sulfoxide-stat-L-alanine), $M^OA$, segments compared to $M^O$ homopolymer (data not shown).

Figure 6:
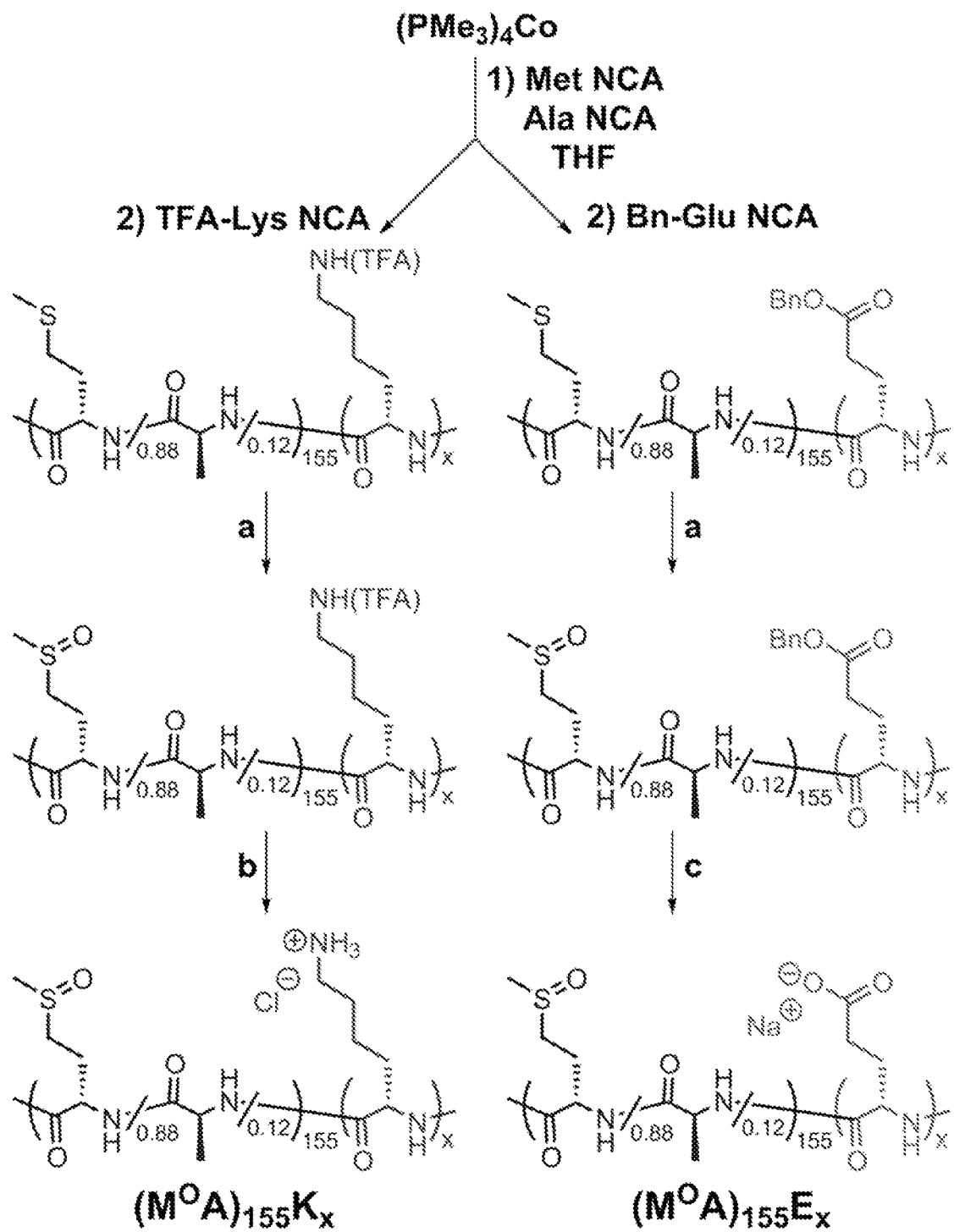
FIG. 6 is a scheme showing a synthesis of oppositely charged, dual hydrophilic diblock copolypeptides $(M^OA)_{155}K_x$ and $(M^OA)_{155}E_x$. a) TBHP, CSA, $H_2O$, 20° C., 1 d. b) $K_2CO_3$, $MeOH/H_2O$, 50° C., 8 h. c) MSA, TFA, anisole, 20° C., 1.5 h.

As examples, diblock copolypeptides containing poly(L-methionine-stat-L-alanine), MA, segments ca. 155 residues long, followed by side-chain protected K or E segments of different length (FIG. 6) were prepared. Subsequent oxidation of M residues, followed by side-chain deprotection of K and E residues and purification gave the target copolypeptides poly(L-methionine sulfoxide-stat-L-alanine)$_{155}$-block-poly(L-lysine-HCl)$_x$, $(M^OA)_{155}K_x$; and poly(L-methionine sulfoxide-stat-L-alanine)$_{155}$-block-poly(L-glutamate-Na)$_x$, $(M^OA)_{155}E_x$, where x=30 (SEQ ID NOS 7 and 10, respectively), 60 (SEQ ID NOS 1 and 2, respectively), 90 (SEQ ID NOS 12 and 8, respectively), and 120 (SEQ ID NOS 13 and 11, respectively) (FIG. 6). All copolymers were isolated in high yield with compositions that closely matched expected values (see Table 1). The K and E lengths were varied in order to study the role of structured PIC domain size on hydrogel formation and properties.

Figures 2A, 2B, 2C, 2D:
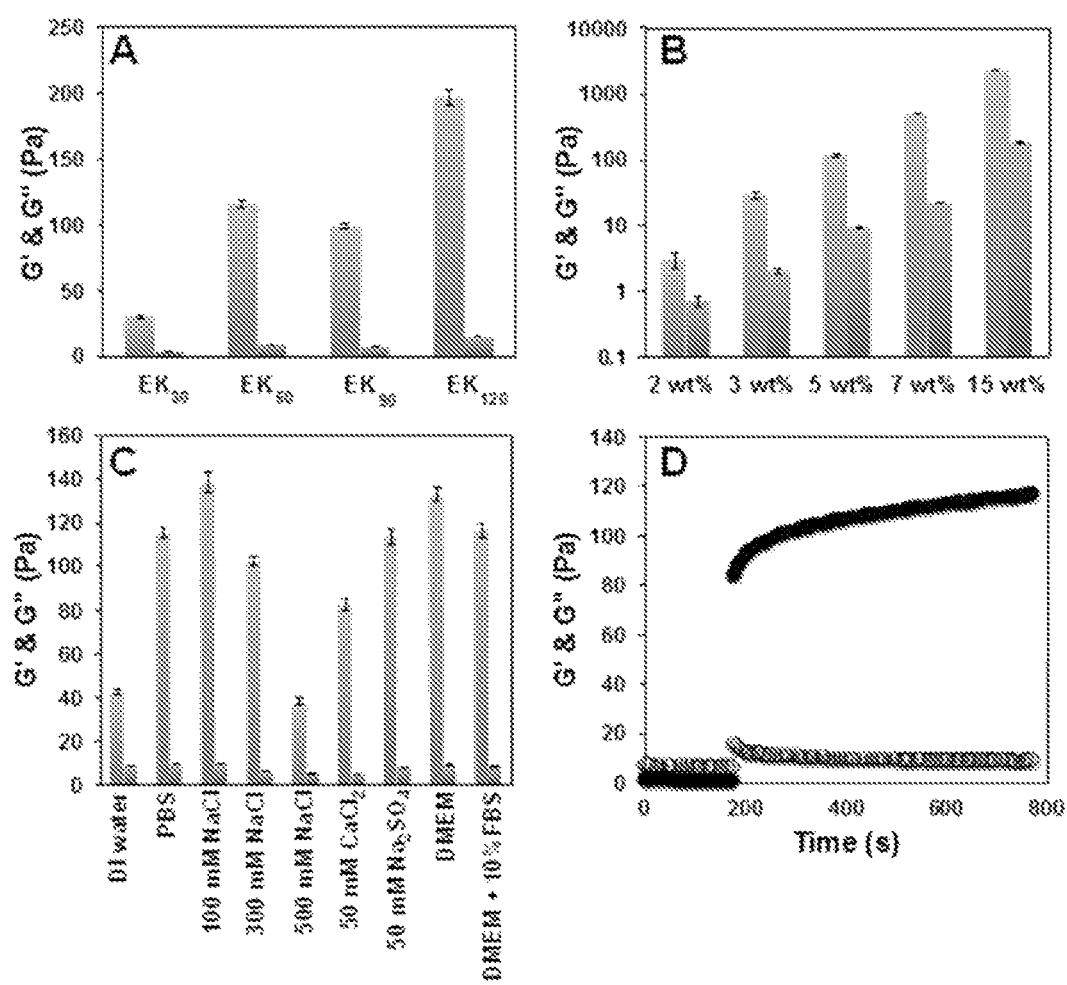
FIG. 2A is a bar graph showing storage modulus, G' (Pa (left bar)), and loss modulus, G" (Pa (right bar)), of hydrogels formed from stoichiometric $(M^OA)_{155}E/K_x$ with different ionic segment lengths (x=30, 60, 90, and 120). Samples (5.0 wt % total combined cationic and anionic copolypeptide) were prepared in 1×PBS buffer at 20° C. G' and G" values were measured at an angular frequency of 5 rad/s and strain amplitude of 0.05.
FIG. 2B is a bar graph showing G' (Pa, (left bar)) and G" (Pa, (right bar)), of $(M^OA)_{155}E/K_{60}$ hydrogels at different concentrations in PBS buffer at 20° C. G' and G" values were measured at an angular frequency of 5 rad/s and strain amplitude of 0.05.
FIG. 2C is a bar graph showing G' (Pa (left bar)) and G" (Pa (right bar)), of 5.0 wt % $(M^OA)_{155}E/K_{60}$ hydrogels prepared in different buffers at 20° C. DMEM=Dulbecco's Modified Eagle Medium; FBS=fetal bovine serum.
FIG. 2D depicts recovery of 5.0 wt % in PBS $(M^OA)_{155}E/K_{60}$ hydrogel properties (G', filled circles; G", open circles) over time after large amplitude oscillatory breakdown (strain amplitude of 10 at 5 rad/s for 200 s), followed by linear recovery measurement (strain amplitude of 0.05 at 5 rad/s). G' and G" values were measured at an angular frequency of 5 rad/s and strain amplitude of 0.05.

For initial evaluation, matching length $(M^OA)_{155}K_x$ and $(M^OA)_{155}E_x$ samples were separately dissolved in aqueous 1×PBS buffer (5.0 wt % of each copolypeptide) to give clear solutions. These solutions were then combined in equal volumes at essentially stoichiometric E to K ratios (ca. 1.02-1.04 to 1) and agitated briefly in a vortex mixer, whereupon all samples (($M^OA)_{155}E/K_x$, x=30, 60, 90, and 120; 5.0 wt % total copolypeptide after mixing) were observed to form hydrogels within 15 seconds to 1 minute. These observations were confirmed by oscillatory rheology measurements where storage moduli (G') were found to dominate over loss moduli (G"), indicating elastic behavior for all samples (FIG. 2A, see Table 2). Mismatched mixtures, prepared either using non-stoichiometric E to K ratios, or by maintaining E to K stoichiometry but combining samples of different length (e.g. three $(M^OA)_{155}K_{30}$ (SEQ ID NO: 7) to one $(M^OA)_{155}E_{90}$ (SEQ ID NO: 8)), were found to give substantially weaker hydrogels compared to corresponding stoichiometric and length-matched samples. Stoichiometric hydrogels prepared using longer $E/K_x$ segments (90 and 120) were opaque, likely due to microscopic aggregate precipitation. Hydrogels prepared using shorter $E/K_x$ segments (30 and 60) were translucent, with only slight turbidity. In general, hydrogel stiffness (G') was found to increase with $E/K_x$ segment length, yet aggregate precipitation with longer segments diminished this trend, as can be seen in G' for the $E/K_{90}$ sample (FIG. 2A). The minimum total copolypeptide concentration required for hydrogel formation was found to be ca. 4.0 wt % for the $(M^OA)_{155}E/K_{30}$ sample, and decreased with increasing $E/K_x$ segment length.

Figures 7A, 7B:
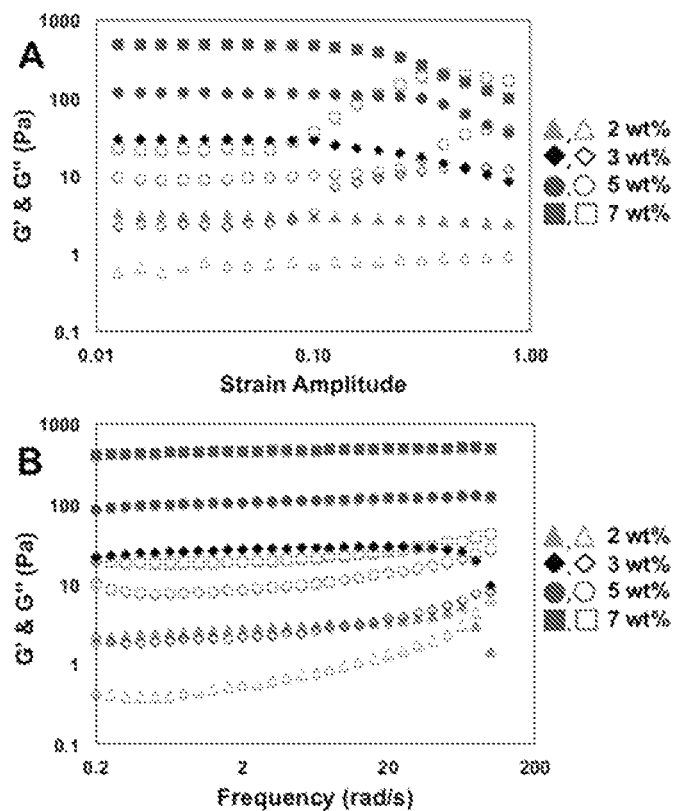
FIG. 7A is a graph of storage modulus, G' (Pa, solid symbols), and loss modulus, G" (Pa, open symbols), of $(M^OA)_{155}E/K_{60}$ hydrogels as functions of strain amplitude at different concentrations in PBS buffer at 20° C. The crossover of G' and G" in the 2.0 and 3.0 wt % samples at high frequency is an artifact attributable to limitations of the measuring geometry (gap loading limit) and should not be considered to be a relaxation time.
FIG. 7B is a graph of G' (Pa, solid symbols) and G" (Pa, open symbols) of $(M^OA)_{155}E/K_{60}$ hydrogels as functions of angular frequency. The crossover of G' and G" in the 2.0 and 3.0 wt % samples at high frequency is an artifact attributable to limitations of the measuring geometry (gap loading limit) and should not be considered to be a relaxation time.

Preparation of hydrogels using different concentrations of $(M^OA)_{155}E/K_{60}$ in 1×PBS was found to be a convenient means to adjust hydrogel stiffness (FIG. 2B). All samples formed elastic hydrogels of similar clarity (G'>>G") over a range of frequency, see FIGS. 7A and 7B), and their stiffness was found to increase with higher copolypeptide concentrations. The lack of visible aggregates in these samples suggests that polymer chains were able to assemble into the desired structures even with fast mixing at high concentrations. $(M^OA)_{155}E/K_{60}$ hydrogels could also be prepared in a variety of aqueous media (FIG. 2C). Solution ionic strengths in the range of ca. 100 to 300 mM were found to be suitable for PIC hydrogel formation, while deionized water and higher salt concentrations (e.g. 500 mM NaCl) resulted in weaker hydrogels. Finally, elevated temperature (80° C. for 1.5 h) was found to have no visible effect on a 5.0 wt % $(M^OA)_{155}E/K_{60}$ hydrogel in 1×PBS, showing that $DCH_{PIC}$ possess good thermal stability.

The self-healing properties of $DCH_{PIC}$ after mechanical breakdown were studied by subjecting a 5.0 wt % $(M^OA)_{155}E/K_{60}$ sample in 1×PBS to high amplitude oscillatory strain, and then monitoring the recovery of elasticity over time by measuring G' at a much smaller strain amplitude (FIG. 2D). During the initial 200 s of high strain amplitude, G' dropped by two orders of magnitude to below the level of G", indicating the sample had become a viscous liquid. Upon switching to low strain amplitude, the sample began recovering its elastic properties, with most of the original gel stiffness regained within the brief period (ca. 10 s) needed to switch between strain amplitudes. Full recovery of $DCH_{PIC}$ elasticity continued to occur over a time scale of minutes. The rapid self-healing ability of $DCH_{PIC}$ would allow for delivery of $DCH_{PIC}$ via injection through small bore needles.

Figures 8A, 8B:
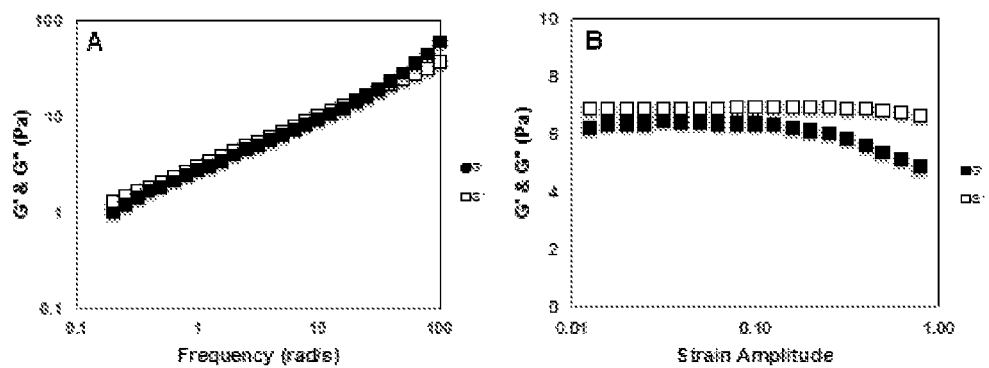
FIG. 8A is a graph of storage modulus G' (solid symbols) and loss modulus G" (open symbols) as a function of angular frequency (strain amplitude of 0.05) for 5.0 wt % $(M^OA)_{155}(rac-E)/K_{60}$ in PBS buffer at 20° C.
FIG. 8B is a graph showing strain sweep at angular frequency of 5 rad/s for 5.0 wt % $(M^OA)_{155}(rac-E)/K_{60}$ in PBS buffer at 20° C.
Figures 9A, 9B, 9C, 9D:
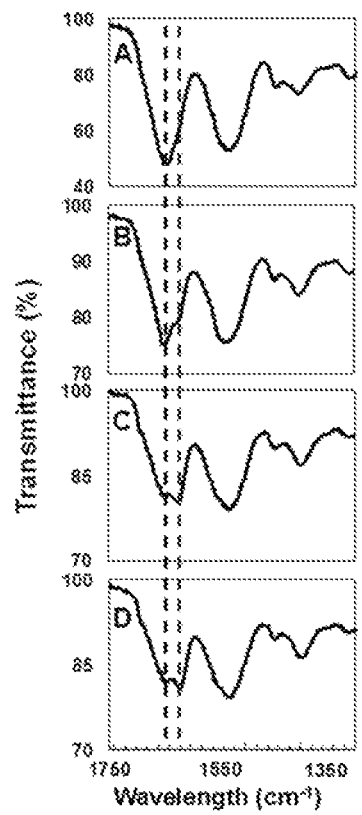
FIG. 9A is an ATR-IR spectrum of a lyophilized $(M^OA)_{155}E/K_{30}$ sample in the amide region. Left dashed line=1653 cm$^{-1}$ Amide I band characteristic of α-helical and disordered chain conformations. Right dashed line=1630 cm$^{-1}$ Amide I band characteristic of β-sheet chain conformations. 1630 cm$^{-1}$ β-sheet Amide I band increases with $E/K_x$ content.
FIG. 9B is an ATR-IR spectrum of a lyophilized $(M^OA)_{155}E/K_{60}$ sample in the amide region. Left dashed line=1653 cm$^{-1}$ Amide I band characteristic of α-helical and disordered chain conformations. Right dashed line=1630 cm$^{-1}$ Amide I band characteristic of β-sheet chain conformations. 1630 cm$^{-1}$ β-sheet Amide I band increases with $E/K_x$ content.
FIG. 9C is an ATR-IR spectrum of a lyophilized $(M^OA)_{155}E/K_{90}$ sample in the amide region. Left dashed line=1653 cm$^{-1}$ Amide I band characteristic of α-helical and disordered chain conformations. Right dashed line=1630 cm$^{-1}$ Amide I band characteristic of β-sheet chain conformations. 1630 cm$^{-1}$ β-sheet Amide I band increases with $E/K_x$ content.
FIG. 9D is an ATR-IR spectrum of a lyophilized $(M^OA)_{155}E/K_{120}$ sample in the amide region. Left dashed line=1653 cm$^{-1}$ Amide I band characteristic of α-helical and disordered chain conformations. Right dashed line=1630 cm$^{-1}$ Amide I band characteristic of β-sheet chain conformations. 1630 cm$^{-1}$ β-sheet Amide I band increases with $E/K_x$ content.
Figures 10A, 10B, 10C, 10D:
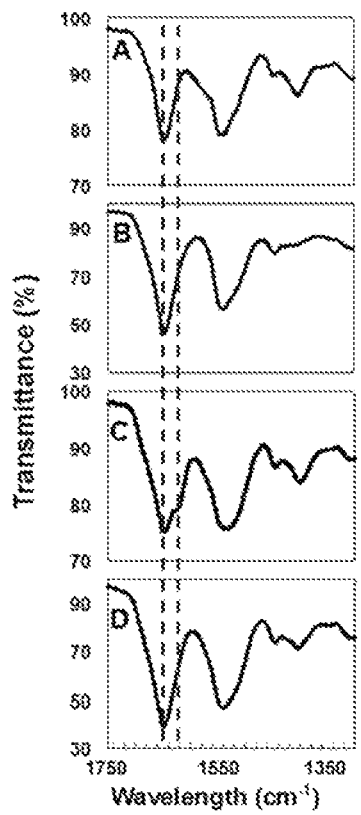
FIG. 10A is an ATR-IR spectrum of a lyophilized sample of $(M^OA)_{155}E_{60}$ (SEQ ID NO: 2). in the amide region. Left dashed line=1653 cm$^{-1}$ Amide I band characteristic of α-helical and disordered chain conformations. Right dashed line=1630 cm$^{-1}$ Amide I band characteristic of β-sheet chain conformations.
FIG. 10B is an ATR-IR spectrum of a lyophilized sample of $(M^OA)_{155}K_{60}$ (SEQ ID NO: 1). in the amide region. Left dashed line=1653 cm$^{-1}$ Amide I band characteristic of α-helical and disordered chain conformations. Right dashed line=1630 cm$^{-1}$ Amide I band characteristic of β-sheet chain conformations.
FIG. 10C is an ATR-IR spectrum of a lyophilized sample of $(M^OA)_{155}E/K_{60}$. in the amide region. Left dashed line=1653 cm$^{-1}$ Amide I band characteristic of α-helical and disordered chain conformations. Right dashed line=1630 cm$^{-1}$ Amide I band characteristic of β-sheet chain conformations. Only $(M^OA)_{155}E/K_{60}$ shows presence of β-sheet content.
FIG. 10D is an ATR-IR spectrum of a lyophilized sample of $(M^OA)_{155}(rac-E)/K_{60}$. in the amide region. Left dashed line=1653 cm$^{-1}$ Amide I band characteristic of α-helical and disordered chain conformations. Right dashed line=1630 cm$^{-1}$ Amide I band characteristic of β-sheet chain conformations.
Figures 11A, 11B:
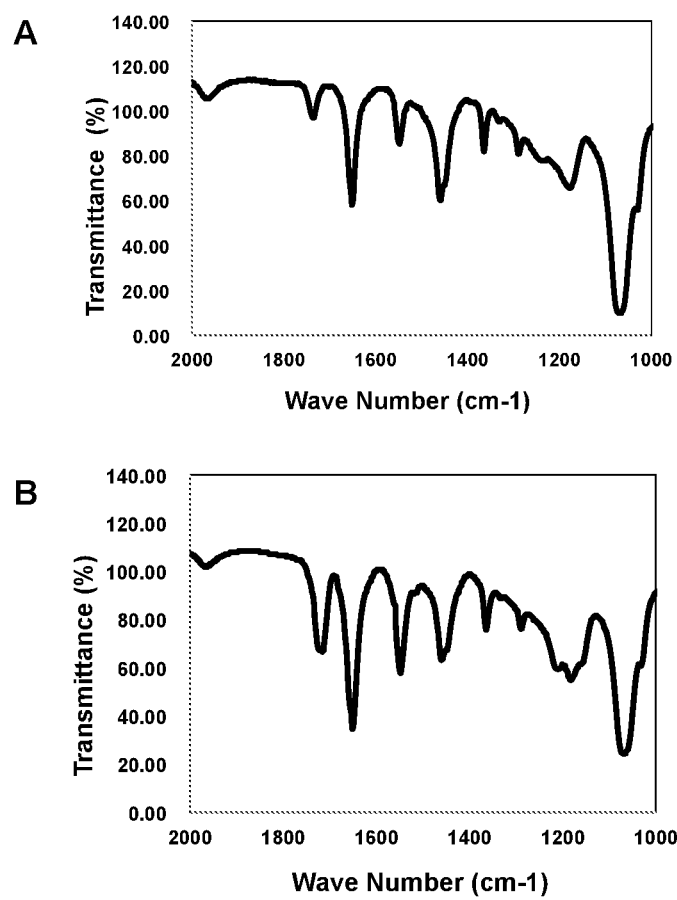
FIG. 11A is an FTIR spectra of $(MA)_{155}(TFA-K)_{120}$ (SEQ ID NO: 4) in THF.
FIG. 11B is an FTIR spectra of $(MA)_{155}(Bn-E)_{120}$ (SEQ ID NO: 5) in THF.
Figure 12:
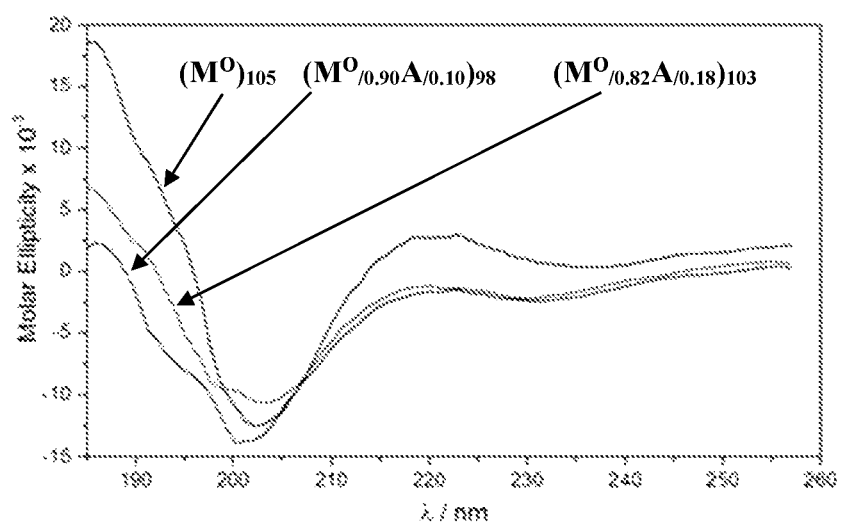
FIG. 12 is a circular dichroism spectrum of $(M^O)_{105}$ (SEQ ID NO: 6), $(M^O_{/0.90}A_{/0.10})_{98}$, and $(M^O_{/0.82}A_{/0.18})_{103}$ polypeptides in DI water at 20° C.

To better understand the assembly of $DCH_{PIC}$, the influence of polyelectrolyte chirality on hydrogel formation was studied. A new copolypeptide component, $(M^OA)_{155}$ (rac-E)$_{60}$ (SEQ ID NO: 9), was prepared, where the rac-E segment was composed of racemic residues. When equivalent amounts of $(M^OA)_{155}$(rac-E)$_{60}$ (SEQ ID NO: 9) and $(M^OA)_{155}K_{60}$ (SEQ ID NO: 1) were mixed (total 5.0 wt % in 1×PBS), the resulting sample did not form a hydrogel and gave only a low viscosity liquid (see FIG. 8A and FIG. 8B). This result confirmed the importance of chirality in formation of $(M^OA)_{155}E/K_{60}$ hydrogel structure. To directly verify the formation of β-sheet assembly in $(M^OA)_{155}E/K_x$ $DCH_{PIC}$, the hydrogels were also analyzed using FTIR, since different polypeptide conformations possess characteristic stretching frequencies for their Amide I and Amide II bands. In FTIR analysis of lyophilized $(M^OA)_{155}E/K_x$ hydrogels (x=30, 60, 90, and 120), all samples possessed strong 1653 cm$^{-1}$ Amide I bands due to the disordered chain conformations of the $(M^OA)$ 155 segments (see FIGS. 9A-9D). The samples also possessed 1630 cm$^{-1}$ Amide I bands, characteristic of β-sheet chain conformations, which increased in intensity as $E/K_x$ segment length increased suggesting that this band resulted from PIC formation (see FIGS. 9A-9D). The β-sheet Amide I band at 1630 cm$^{-1}$ was only present in the homochiral $(M^OA)_{155}E/K_x$ PICs, and was absent in the individual components as well as the $(M^OA)_{155}$(rac-E)/K$_{60}$ PIC formed with a racemic component (see FIGS. 10A-10D). Together, these data confirmed that the K and E segments in $(M^OA)_{155}E/K_x$ PIC are assembling as β-sheets.

Figures 3A, 3B, 3C, 3D:
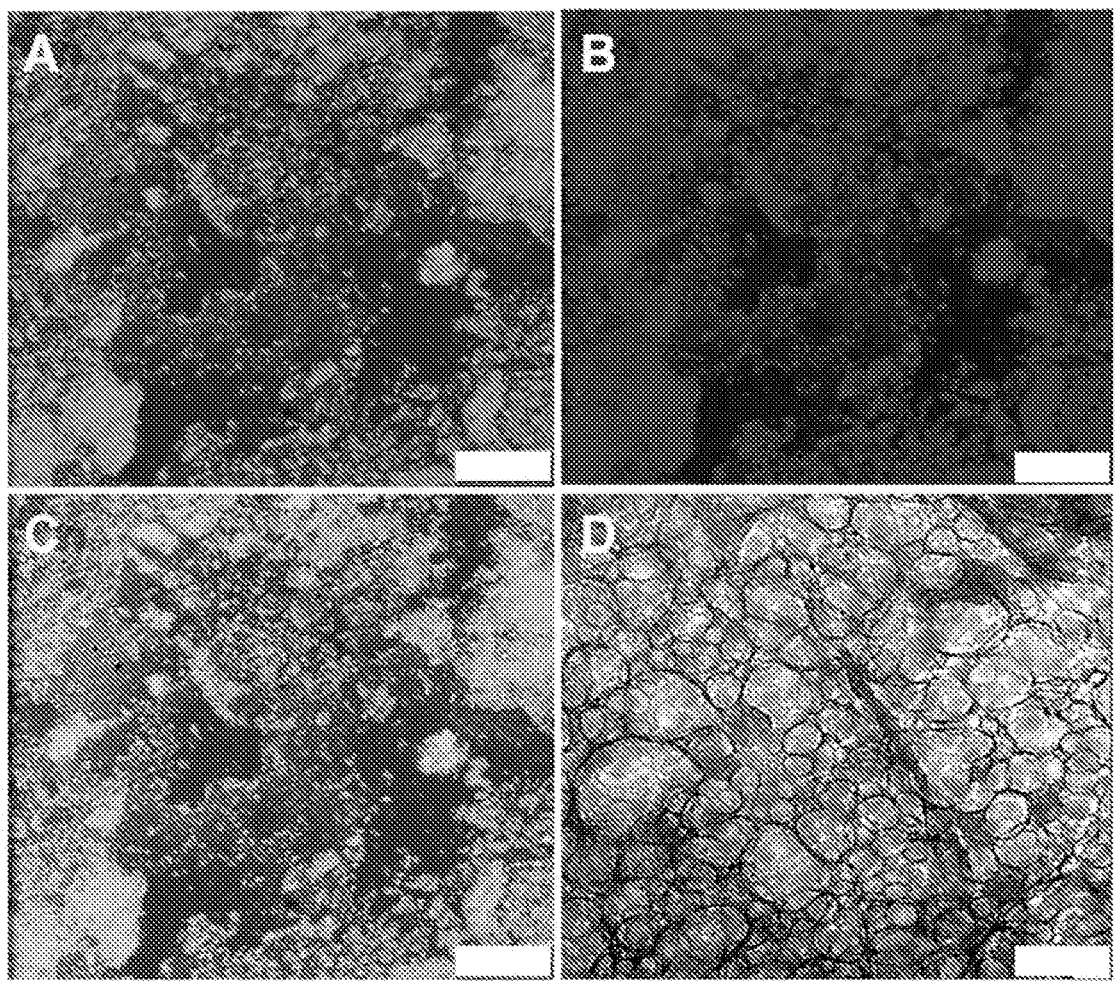
FIG. 3A is a laser scanning confocal microscopy (LSCM) image of $(M^OA)_{155}E/K_{60}$ hydrogels (z-thickness=0.78 μm) of TRITC labeled $(M^OA)_{155}K_{60}$ (SEQ ID NO: 1) and FITC labeled $(M^OA)_{155}E_{60}$ (SEQ ID NO: 2) hydrogel mixtures showing microporous structure (3.0 wt % in PBS) observed via a FITC channel. Scale bars=25 μm.
FIG. 3B is a laser scanning confocal microscopy (LSCM) image of $(M^OA)_{155}E/K_{60}$ hydrogels (z-thickness=0.78 μm) of TRITC labeled $(M^OA)_{155}K_{60}$ (SEQ ID NO: 1) and FITC labeled $(M^OA)_{155}E_{60}$ (SEQ ID NO: 2) hydrogel mixtures showing microporous structure (3.0 wt % in PBS) observed via a TRITC channel. Scale bars=25 μm.
FIG. 3C is a merged image of FIG. 3A and FIG. 3B. Scale bars=25 μm.
FIG. 3D is a cryoelectron microscopy (cryoEM) image of $(M^OA)_{155}E/K_{60}$ hydrogel showing nanoporous structure (2.0 wt % in PBS). Scale bars=200 nm.

The supramolecular structure of $(M^OA)_{155}E/K_{60}$ hydrogels was analyzed at both microscale and nanoscale resolution. To visualize microscopic structure, chains of $(M^OA)_{155}E_{60}$ (SEQ ID NO: 2) and $(M^OA)_{155}K_{60}$ (SEQ ID NO: 1) were separately conjugated with different fluorescent probes (tetramethylrhodamine and fluorescein, respectively) and then mixed to form $DCH_{PIC}$. Laser scanning confocal microscopy (LSCM) was then used to visualize the labeled chains and the hydrogel network (FIG. 3A-3B). Both K labeled (TRITC) and E labeled (FITC) channels showed $DCH_{PIC}$ are composed of microporous networks containing interconnected polypeptide rich domains that coexist with domains primarily composed of water, seen as dark regions in the images. An overlay of the channels revealed that K and E segments are co-localized, indicating good mixing of the components within the $DCH_{PIC}$ domains (FIG. 3C). Cryo electron microscopy (cryoEM) imaging of a thin layer of vitrified $(M^OA)_{155}E/K_{60}$ hydrogel showed structures resembling "plumber's nightmare" morphologies, which consist of membrane like regions interconnected with fibrillar struts, and contain many defects that form a nanoporous network (FIG. 3D).

Figures 4A, 4B, 4C, 4D:
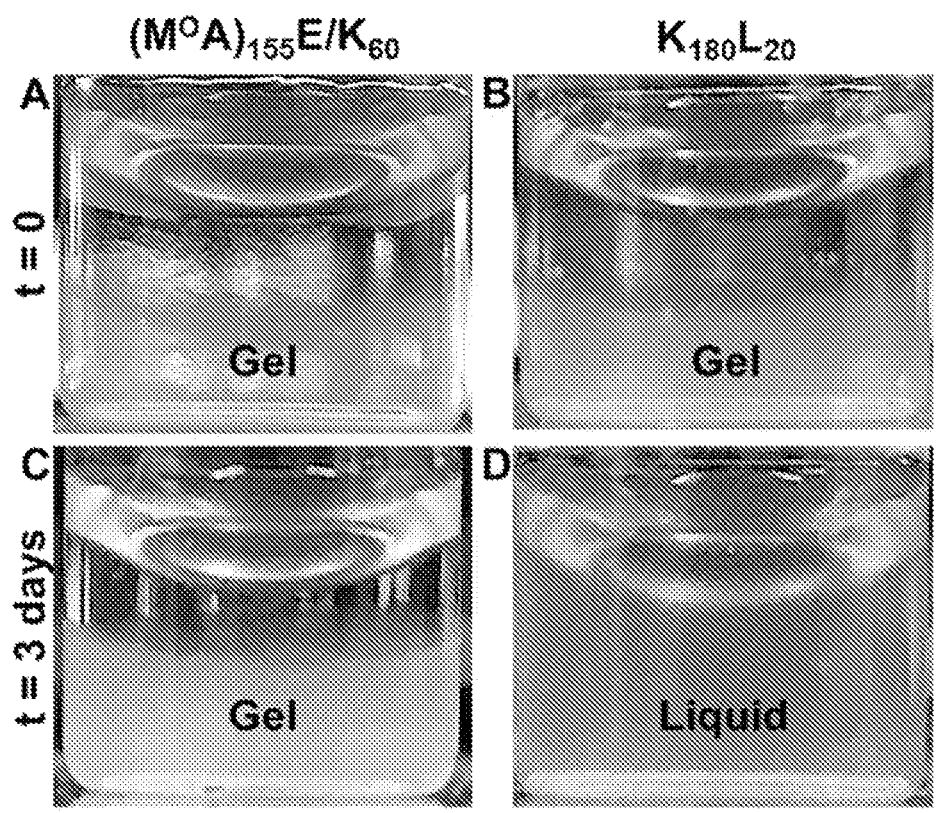
FIG. 4A is a photograph showing, at the beginning of the experiment (time=0), a layer of cell media formed over a polyion complex $(M^OA)_{155}E/K_{55}$ (5.0 wt %) hydrogel (G'≈120 Pa) in 1×PBS diluted with an equal volume of DMEM cell culture media.
FIG. 4B is a photograph showing, at the beginning of the experiment (time=0), a layer of cell media formed over a hydrophobic assembled $K_{180}L_{20}$ (SEQ ID NO: 3) (2.0 wt %) hydrogel (G'≈120 Pa) in 1×PBS diluted with an equal volume of DMEM cell culture media.
FIG. 4C is a photograph showing, after 3 days, the $(M^OA)_{155}E/K_{60}$ hydrogel of FIG. 4A intact.
FIG. 4D is a photograph showing, after 3 days, the $K_{180}L_{20}$ (SEQ ID NO: 3) hydrogel of FIG. 4B dispersed into the full volume of media.

To study the stability of $DCH_{PIC}$ against dilution in aqueous media, a 5.0 wt % $(M^OA)_{155}E/K_{60}$ hydrogel in PBS was prepared, and then an equal volume of DMEM cell culture media was added on top of the hydrogel (FIG. 4A). For comparison, a similar experiment was performed using a 2.0 wt % $K_{180}L_{20}$ (SEQ ID NO: 3) hydrogel in PBS (FIG. 4B), where its concentration was chosen to match the stiffness of the $(M^OA)_{155}E/K_{60}$ hydrogel. Initially, the DMEM solutions formed clear layers above both hydrogels. After 3 days, the $K_{180}L_{20}$ (SEQ ID NO: 3) sample had fully mixed with the DMEM layer and the diluted sample was a viscous liquid. With $(M^OA)_{155}E/K_{60}$, although the DMEM solutes were able to diffuse into the sample over 3 days, the hydrogel was able to retain its shape and stiffness (FIG. 4C-4D). The combination of H-bonding and electrostatic interactions present in the assemblies of $DCH_{PIC}$ was found to impart strong resistance against dissolution in aqueous media.

Figures 5A, 5B, 5C, 5D:
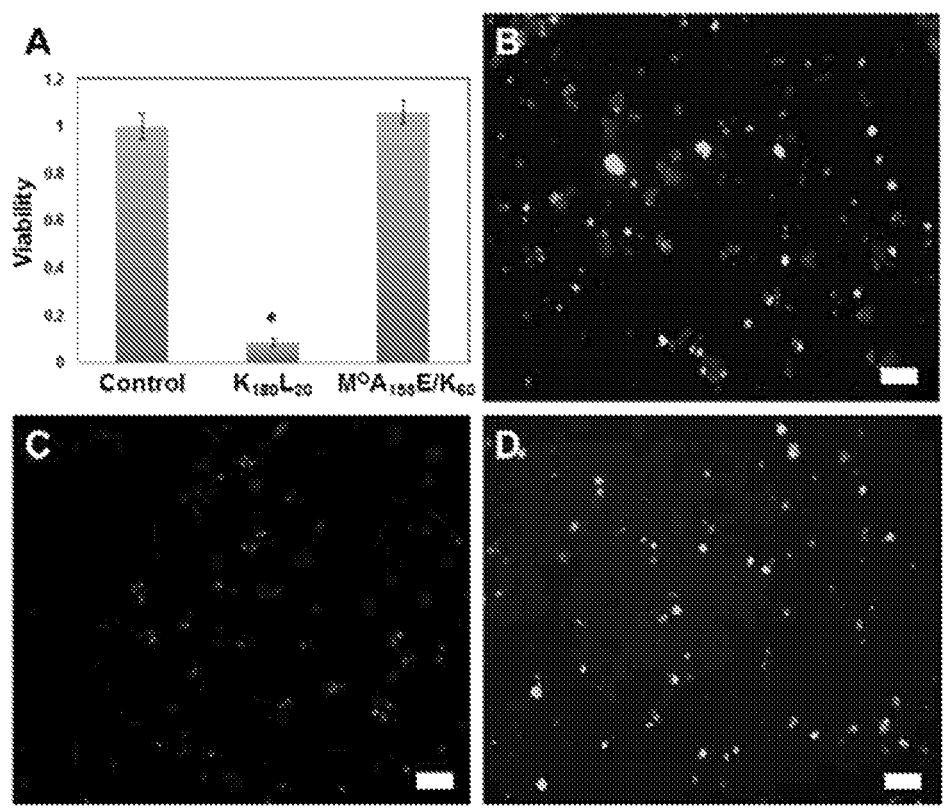
FIG. 5A is a plot of NSPC viability after 1 day incubation in different conditions: cells in media only control, in media plus 2.0 wt % $K_{180}L_{20}$ (SEQ ID NO: 3) hydrogel, or in media plus 5.0 wt % $(M^OA)_{155}E/K_{60}$ hydrogel.
FIG. 5B is a fluorescence microscopy image of NSPC cells after 1 day incubation in media only control and then stained using the Live/Dead® viability/cytotoxicity assay where the light spots are due to calcein (live cells) and darker spots are due to EthD-1 (dead cells). Scale bars=100 μm. * p<0.0001 (Unpaired student's t-test for $K_{180}L_{20}$ (SEQ ID NO: 3) with either cell control or $(M^OA)_{155}E/K_{60}$).
FIG. 5C is a fluorescence microscopy image of NSPC cells after 1 day incubation in media plus 2.0 wt % $K_{180}L_{20}$ (SEQ ID NO: 3) hydrogel and then stained using the Live/Dead® viability/cytotoxicity assay where the light spots are due to calcein (live cells) and darker spots are due to EthD-1 (dead cells). Scale bars=100 μm. * p<0.0001 (Unpaired student's t-test for $K_{180}L_{20}$ (SEQ ID NO: 3) with either cell control or $(M^OA)_{155}E/K_{60}$).
FIG. 5D is a fluorescence microscopy image of NSPC cells after 1 day incubation in media plus 5.0 wt % $(M^OA)_{155}E/K_{60}$ hydrogel and then stained using the Live/Dead® viability/cytotoxicity assay where the light spots are due to calcein (live cells) and darker spots are due to EthD-1 (dead cells). Scale bars=100 μm. * p<0.0001 (Unpaired student's t-test for $K_{180}L_{20}$ (SEQ ID NO: 3) with either cell control or $(M^OA)_{155}E/K_{60}$).

The ability of $DCH_{PIC}$ to resist dissolution or swelling once formed provides a means to cast hydrogel shapes from precursor solutions, and then use these stable hydrogels for various applications in aqueous media. To showcase their potential utility, we encapsulated primary neural stem progenitor cells (NSPCs) in a $(M^OA)_{155}E/K_{60}$ hydrogel (FIG. 5). The NSPCs were encapsulated by mixing a suspension of cells in media with an equal volume of $(M^OA)_{155}E_{60}$ (SEQ ID NO: 2) solution in media, which was then combined with an equal volume of $(M^OA)_{155}K_{60}$ (SEQ ID NO: 1) solution in media to rapidly form the cell containing hydrogel. This sample, as well as cell only and cell in $K_{180}L_{20}$ (SEQ ID NO: 3) hydrogel controls in media, was incubated for 1 day, and then cell viability was quantified using a Live/Dead assay (FIG. 5). The cationic $K_{180}L_{20}$ (SEQ ID NO: 3) hydrogel was found to be cytotoxic in this experiment, and served as a good negative control. The $(M^OA)_{155}E/K_{60}$ hydrogel provided good cell viability, similar to the cells in media only control, which suggests that $DCH_{PIC}$ may be promising for use a cell carrier. Although $DCH_{PIC}$ contain long, charged polypeptide segments, these are effectively sequestered by PIC formation and steric shielding from the uncharged $M^OA$ hydrophilic segments, resulting in hydrogels that are effectively non-ionic. Although cells were exposed to the non-complexed, charged components of $DCH_{PIC}$ during the mixing process, this brief exposure, regardless of mixing order, was found to have minimal adverse effects on cell viability.

Exemplary Compositions

In certain embodiments, the invention relates to a composition comprising, consisting essentially of, or consisting of a first copolypeptide comprising, consisting essentially of, or consisting of Substructure I, a second copolypeptide comprising, consisting essentially of, or consisting of Substructure II, and water, wherein Substructure I is depicted as follows:

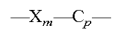  Substructure I;

Substructure II is depicted as follows:

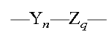  Substructure II;

each instance of X is an amino acid residue independently selected from a non-ionic, hydrophilic amino acid, glycine, and alanine;

each instance of Y is an amino acid residue independently selected from a non-ionic, hydrophilic amino acid, glycine, and alanine;

each instance of C is an amino acid residue independently selected from a cationic, hydrophilic amino acid;

each instance of Z is an amino acid residue independently selected from an anionic, hydrophilic amino acid;

m is about 100 to about 600;

n is about 100 to about 600;
p is about 20 to about 200;
q is about 20 to about 200;
at least 90 mol % of the C amino acid residues are (D)-amino acid residues or at least 90 mol % of the C amino acid residues are (L)-amino acid residues; and
at least 90 mol % of the Z amino acid residues are (D)-amino acid residues or at least 90 mol % of the Z amino acid residues are (L)-amino acid residues.

In certain embodiments, the invention relates to any of the compositions described herein, wherein the first copolypeptide comprises only amino acid residues. In certain embodiments, the invention relates to any of the compositions described herein, wherein the second copolypeptide comprises only amino acid residues. In certain embodiments, the invention relates to any of the compositions described herein, wherein the first copolypeptide and the second copolypeptide comprise only amino acid residues.

In certain embodiments, the invention relates to any of the compositions described herein, wherein the first copolypeptide does not comprise PEG. In certain embodiments, the invention relates to any of the compositions described herein, wherein the second copolypeptide does not comprise PEG. In certain embodiments, the invention relates to any of the compositions described herein, wherein the first copolypeptide and the second copolypeptide do not comprise PEG.

In certain embodiments, the invention relates to any of the compositions described herein, wherein the first copolypeptide is a diblock copolypeptide. In certain embodiments, the invention relates to any of the compositions described herein, wherein the second copolypeptide is a diblock copolypeptide. In certain embodiments, the invention relates to any of the compositions described herein, wherein the first copolypeptide and the second copolypeptide are diblock copolypeptides.

In certain embodiments, the invention relates to any of the compositions described herein, wherein —$X_m$— has a primarily disordered configuration, for example, a configuration that is less than about 20% helical or less than about 20% beta-sheet.

In certain embodiments, the invention relates to any of the compositions described herein, wherein —$Y_n$— has a primarily disordered configuration, for example, a configuration that is less than about 20% helical or less than about 20% beta-sheet.

In certain embodiments, wherein each instance of X is an amino acid residue independently selected from methionine sulfoxide, S-alkyl-cysteine sulfoxide, S-alkyl cysteine sulfone, glycosylated cysteine, serine, homoserine, homomethionine sulfoxide, glycine, and alanine.

In certain embodiments, the invention relates to any of the compositions described herein, wherein each instance of Y is an amino acid residue independently selected from methionine sulfoxide, S-alkyl-cysteine sulfoxide, S-alkyl cysteine sulfone, glycosylated cysteine, serine, homoserine, homomethionine sulfoxide, glycine, and alanine.

In certain embodiments, the invention relates to a composition comprising a first copolypeptide comprising Substructure I, a second copolypeptide comprising Substructure II, and water,
wherein
Substructure I is depicted as follows:

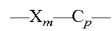  Substructure I;

Substructure II is depicted as follows:

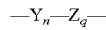  Substructure II;

each instance of X is an amino acid residue independently selected from methionine sulfoxide, S-alkyl-cysteine sulfoxide, S-alkyl cysteine sulfone, glycosylated cysteine, serine, homoserine, homomethionine sulfoxide, glycine, and alanine;
each instance of Y is an amino acid residue independently selected from methionine sulfoxide, S-alkyl-cysteine sulfoxide, S-alkyl cysteine sulfone, glycosylated cysteine, serine, homoserine, homomethionine sulfoxide, glycine, and alanine;
each instance of C is an amino acid residue independently selected from lysine and arginine;
each instance of Z is an amino acid residue independently selected from glutamic acid and aspartic acid;
m is about 100 to about 600;
n is about 100 to about 600;
p is about 20 to about 200;
q is about 20 to about 200;
at least 90 mol % of the C amino acid residues are (D)-amino acid residues or at least 90 mol % of the C amino acid residues are (L)-amino acid residues; and
at least 90 mol % of the Z amino acid residues are (D)-amino acid residues or at least 90 mol % of the Z amino acid residues are (L)-amino acid residues.

In certain embodiments, the invention relates to any of the compositions described herein, wherein the first copolypeptide, the second copolypeptide, and the water are in admixture.

In certain embodiments, the invention relates to any of the compositions described herein, wherein —$X_m$— has a primarily disordered configuration, for example, a configuration that is less than about 20% helical or less than about 20% beta-sheet.

In certain embodiments, the invention relates to any of the compositions described herein, wherein —$Y_n$— has a primarily disordered configuration, for example, a configuration that is less than about 20% helical or less than about 20% beta-sheet.

In certain embodiments, the invention relates to any of the compositions described herein, wherein at least 80 mol % of the X amino acid residues are a sulfur-containing amino acid.

In certain embodiments, the invention relates to any of the compositions described herein, wherein at least 80 mol % of the Y amino acid residues are a sulfur-containing amino acid.

In certain embodiments, the invention relates to any of the compositions described herein, wherein at least 80 mol % of the X amino acid residues are methionine sulfoxide.

In certain embodiments, wherein at least 90 mol % of the X amino acid residues are (D)-amino acid residues or at least 90 mol % of the X amino acid residues are (L)-amino acid residues.

In certain embodiments, the invention relates to any of the compositions described herein, wherein at least 90 mol % of the X amino acid residues are (D)-amino acid residues.

In certain embodiments, the invention relates to any of the compositions described herein, wherein at least 90 mol % of the X amino acid residues are (L)-amino acid residues.

In certain embodiments, the invention relates to any of the compositions described herein, wherein at least 85 mol % of the X amino acid residues are methionine sulfoxide.

In certain embodiments, the invention relates to any of the compositions described herein, wherein at least 85 mol % of the X amino acid residues are methionine sulfoxide, and the remaining X amino acid residues are alanine.

In certain embodiments, the invention relates to any of the compositions described herein, wherein about 88 mol % of the X amino acid residues are methionine sulfoxide, and about 12 mol % of the X amino acid residues are alanine.

In certain embodiments, the invention relates to any of the compositions described herein, wherein at least 80 mol % of the Y amino acid residues are methionine sulfoxide.

In certain embodiments, the invention relates to any of the compositions described herein, wherein at least 90 mol % of the Y amino acid residues are (D)-amino acid residues or at least 90% of the Y amino acid residues are (L)-amino acid residues.

In certain embodiments, the invention relates to any of the compositions described herein, wherein at least 90 mol % of the Y amino acid residues are (D)-amino acid residues.

In certain embodiments, the invention relates to any of the compositions described herein, wherein at least 90% of the Y amino acid residues are (L)-amino acid residues.

In certain embodiments, the invention relates to any of the compositions described herein, wherein at least 85 mol % of the Y amino acid residues are methionine sulfoxide.

In certain embodiments, wherein at least 85 mol % of the Y amino acid residues are methionine sulfoxide, and the remaining Y amino acid residues are alanine.

In certain embodiments, the invention relates to any of the compositions described herein, wherein about 88 mol % of the Y amino acid residues are methionine sulfoxide, and about 12 mol % of the Y amino acid residues are alanine.

In certain embodiments, the invention relates to any of the compositions described herein, wherein at least 90% of the C amino acid residues are (D)-amino acid residues.

In certain embodiments, the invention relates to any of the compositions described herein, wherein at least 90% of the C amino acid residues are (L)-amino acid residues.

In certain embodiments, the invention relates to any of the compositions described herein, wherein each instance of C is lysine.

In certain embodiments, the invention relates to any of the compositions described herein, wherein each instance of C is (L)-lysine.

In certain embodiments, the invention relates to any of the compositions described herein, wherein each instance of C is (D)-lysine.

In certain embodiments, the invention relates to any of the compositions described herein, wherein at least 90% of the Z amino acid residues are (D)-amino acid residues.

In certain embodiments, the invention relates to any of the compositions described herein, wherein at least 90% of the Z amino acid residues are (L)-amino acid residues.

In certain embodiments, the invention relates to any of the compositions described herein, wherein each instance of Z is glutamic acid.

In certain embodiments, the invention relates to any of the compositions described herein, wherein each instance of Z is (L)-glutamic acid.

In certain embodiments, the invention relates to any of the compositions described herein, wherein each instance of Z is (D)-glutamic acid.

In certain embodiments, wherein m is about 100, about 110, about 120, about 130, about 140, about 150, about 160, about 170, about 180, about 190, about 200, about 210, or about 220.

In certain embodiments, the invention relates to any of the compositions described herein, wherein m is about 120, about 130, about 140, about 150, about 160, about 170, about 180, or about 190.

In certain embodiments, the invention relates to any of the compositions described herein, wherein n is about 100, about 110, about 120, about 130, about 140, about 150, about 160, about 170, about 180, about 190, about 200, about 210, or about 220.

In certain embodiments, the invention relates to any of the compositions described herein, wherein n is about 120, about 130, about 140, about 150, about 160, about 170, about 180, or about 190.

In certain embodiments, the invention relates to any of the compositions described herein, wherein p is about 20, about 30, about 40, about 50, about 60, about 70, about 80, about 90, about 100, about 110, about 120, or about 130.

In certain embodiments, the invention relates to any of the compositions described herein, wherein q is about 20, about 30, about 40, about 50, about 60, about 70, about 80, about 90, about 100, about 110, about 120, or about 130.

In certain embodiments, the invention relates to any of the compositions described herein, wherein the polydispersity of the first copolypeptide is less than 1.5.

In certain embodiments, the invention relates to any of the compositions described herein, wherein the polydispersity of the second copolypeptide is less than 1.5.

In certain embodiments, the invention relates to any of the compositions described herein, wherein the number of amino acid residues in the first copolypeptide is from about 90% to about 110% of the number of amino acid residues in the second copolypeptide.

In certain embodiments, the invention relates to any of the compositions described herein, wherein the total concentration of the first copolypeptide and the second copolypeptide in the composition is greater than about 2.0 wt. %.

In certain embodiments, wherein the total concentration of the first copolypeptide and the second copolypeptide in the composition is greater than about 3.0 wt. %.

In certain embodiments, the invention relates to any of the compositions described herein, wherein the total concentration of the first copolypeptide and the second copolypeptide in the composition is greater than about 4.0 wt. %.

In certain embodiments, the invention relates to any of the compositions described herein, wherein the total concentration of the first copolypeptide and the second copolypeptide in the composition is about 5.0 wt. %

In certain embodiments, the invention relates to any of the compositions described herein, wherein the molar ratio of C to Z is from about 0.95 to about 1.05.

In certain embodiments, the invention relates to any of the compositions described herein, wherein the molar ratio of X to Y is from about 0.95 to about 1.05.

In certain embodiments, the invention relates to any of the compositions described herein, wherein the composition further comprises a salt.

In certain embodiments, the invention relates to any of the compositions described herein, wherein the concentration of the salt in the composition is less than about 500 mM.

In certain embodiments, the invention relates to any of the compositions described herein, wherein the concentration of the salt in the composition is from about 100 mM to about 300 mM.

In certain embodiments, the invention relates to any of the compositions described herein, wherein the salt is NaCl.

In certain embodiments, the invention relates to any of the compositions described herein, wherein the composition further comprises a buffer.

In some embodiments, the composition comprises $(M^OA)_{155}E_{30}$ (SEQ ID NO: 10), $(M^OA)_{155}E_{60}$ (SEQ ID NO: 2), $(M^OA)_{155}E_{90}$ (SEQ ID NO: 8), $(M^OA)_{155}E_{120}$ (SEQ ID NO: 11). $(M^OA)_{155}(rac-E)_{60}$ (SEQ ID NO: 9). $(M^OA)_{155}K_{30}$ (SEQ ID NO: 7), $(M^OA)_{155}K_{60}$ (SEQ ID NO: 1). $(M^OA)_{155}K_{90}$ (SEQ ID NO: 12), or $(M^OA)_{155}K_{120}$ (SEQ ID NO: 13).

In some embodiments, the composition comprises $(M^OA)_{155}E_{30}$ (SEQ ID NO: 10).

In some embodiments, the composition comprises $(M^OA)_{155}E_{60}$ (SEQ ID NO: 2).

In some embodiments, the composition comprises $(M^OA)_{155}E_{90}$ (SEQ ID NO: 8).

In some embodiments, the composition comprises $(M^OA)_{155}E_{120}$ (SEQ ID NO: 11).

In some embodiments, the composition comprises $(M^OA)_{155}(rac-E)_{60}$ (SEQ ID NO: 9).

In some embodiments, the composition comprises $(M^OA)_{155}K_{30}$ (SEQ ID NO: 7).

In some embodiments, the composition comprises $(M^OA)_{155}K_{60}$ (SEQ ID NO: 1).

In some embodiments, the composition comprises $(M^OA)_{155}K_{90}$ (SEQ ID NO: 12).

In some embodiments, the composition comprises $(M^OA)_{155}K_{120}$ (SEQ ID NO: 13).

In certain embodiments, the invention relates to any of the compositions described herein, wherein the composition further comprises a plurality of cells.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The definition of each expression, e.g., alkyl, m, n, and the like, when it occurs more than once in any structure, is intended to be independent of its definition elsewhere in the same structure.

Certain compounds contained in compositions of the invention may exist in particular geometric or stereoisomeric forms. In addition, polymers of the invention may also be optically active. The invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

For purposes of this invention, the chemical elements are identified in accordance with the Periodic Table of the Elements, CAS version, Handbook of Chemistry and Physics, 67th Ed., 1986-87, inside cover.

EXEMPLIFICATION

The following examples include experimental procedures and spectral data for sample compounds, procedures for alkylation reactions, and methods for stability studies.

General Materials and Methods for all Examples

Materials and Instrumentation.

Tetrahydrofuran (THF), hexanes, and methylene chloride were dried by purging with nitrogen and passage through activated alumina columns prior to use. $Co(PMe_3)_4$ and amino acid N-carboxyanhydride (NCA) monomers were prepared according to literature procedures. Kramer, J. R.; Deming, T. J. *Biomacromolecules* 2012, 13, 1719-1723. All other chemicals were purchased from commercial suppliers and used without further purification unless otherwise noted. Selecto silica gel 60 (particle size 0.032-0.063 mm) was used for flash column chromatography. Fourier Transform Infrared (FTIR) measurements were taken on a Perkin Elmer RX1 FTIR spectrophotometer calibrated using polystyrene film, and attenuated total reflectance (ATR-IR) data were collected using a PerkinElmer Spectrum 100 FTIR spectrometer equipped with a universal ATR sample accessory. 1H NMR spectra were acquired on a Bruker ARX 400 spectrometer. Tandem gel permeation chromatography/light scattering (GPC/LS) was performed at 25° C. using an SSI Accuflow Series III pump equipped with Wyatt DAWN EOS light scattering and Optilab REX refractive index detectors. Separations were achieved using 100 Å and 1000 Å PSS-PFG 7 µm columns at 30° C. with 0.5% (w/w) KTFA in 1,1,1,3,3,3-hexafluoroisopropanol (HFIP) as eluent and sample concentrations of 10 mg/ml. Pyrogen free deionized water (DI) was obtained from a Millipore Milli-Q Biocel A10 purification unit. Circular Dichroism spectra were recorded in quartz cuvettes of 0.1 cm path length with samples prepared at concentrations between 0.10 to 0.17 mg/mL using Millipore deionized water. The spectra are reported in units of molar ellipticity [θ] (deg·cm$^2$·dmol$^{-1}$), using the formula, [θ]=(θ×100×Mw)/(c×l), where θ is the measured ellipticity in millidegrees, Mw, is the average residue molecular mass in g/mol, c is the peptide concentration in mg/ml; and l is the cuvette path length in cm.

General Procedure for Copolypeptide Preparation

All polymerization reactions were performed in an $N_2$ filled glove box using anhydrous solvents. To a solution of L-methionine NCA (Met NCA) and L-alanine NCA (Ala NCA) in THF (50 mg/ml), a solution of Co(PMe$_3$)$_4$ in THF (20 mg/ml) was added. The reaction was let to stir at ambient temperature (ca. 22° C.) for 60 min. Complete consumption of NCA was confirmed by FTIR spectroscopy, and then the desired amount of γ-benzyl-L-glutamate NCA (Bn-Glu NCA) or ε-TFA-L-lysine NCA (TFA-Lys NCA) in THF (50 mg/ml) was added to the reaction mixture, which was let to stir for an additional 60 min. FTIR was used to confirm complete consumption of all NCAs. Outside the glove box, the block copolypeptide solutions were precipitated into 10 mM HCl (20 ml), and then washed with 10 mM aqueous HCl (2×20 ml) to remove residual cobalt ions. The white precipitates were then washed with DI water (3×20 ml) and freeze-dried.

TABLE 1

Copolymerization data for diblock copolypeptide synthesis.

| Sample | SEQ ID NO: | $M_w/M_n^a$ | Composition$^b$ | SEQ ID NO: | Yield (%)$^c$ |
|---|---|---|---|---|---|
| $(M^OA)_{155}E_{30}$ | 10 | 1.35 | $(M^OA)_{156}E_{27}$ | 14 | 94 |
| $(M^OA)_{155}E_{60}$ | 2 | 1.41 | $(M^OA)_{156}E_{59}$ | 15 | 96 |
| $(M^OA)_{155}E_{90}$ | 8 | 1.45 | $(M^OA)_{156}E_{88}$ | 16 | 92 |
| $(M^OA)_{155}E_{120}$ | 11 | 1.42 | $(M^OA)_{156}E_{117}$ | 17 | 97 |
| $(M^OA)_{155}(rac-E)_{60}$ | 9 | 1.45 | $(M^OA)_{156}(rac-E)_{56}$ | 18 | 92 |
| $(M^OA)_{155}K_{30}$ | 7 | 1.38 | $(M^OA)_{156}K_{28}$ | 19 | 97 |
| $(M^OA)_{155}K_{60}$ | 1 | 1.41 | $(M^OA)_{156}K_{62}$ | 20 | 95 |
| $(M^OA)_{155}K_{90}$ | 12 | 1.40 | $(M^OA)_{156}K_{88}$ | 21 | 95 |
| $(M^OA)_{155}K_{120}$ | 13 | 1.37 | $(M^OA)_{156}K_{119}$ | 22 | 96 |

$^a$Dispersity of oxidized, protected block copolypeptides were determined by GPC/LS.
$^b$Relative amino acid compositions of oxidized, deprotected block copolypeptides were determined by $^1$H NMR integrations. Degree of polymerization of initial MA$_x$ segment was determined by end-group analysis using $^1$H NMR.
$^c$Total isolated yield of purified block copolypeptides following deprotection.

Example Synthesis of poly(L-methionine$_{0.88}$-stat-L-alanine$_{0.12}$)$_{155}$-block-poly(ε-trifluoroacetyl-L-lysine)$_{60}$ (SEQ ID NO: 23), (MA)$_{155}$(TFA-K)$_{55}$ (SEQ ID NO: 24) and poly(L-methionine$_{0.88}$-stat-L-alanine$_{0.12}$)$_{155}$-block-poly(γ-benzyl-L-glutamate)$_{60}$ (SEQ ID NO: 25), (MA)$_{155}$(Bn-E)$_{60}$ (SEQ ID NO: 26)

Met NCA (120 mg, 0.71 mmol) and Ala NCA (11 mg, 0.097 mmol) were dissolved together in THF (2.7 ml) and placed in a 20 ml scintillation vial containing a stir bar. To the vial, (PMe$_3$)$_4$Co initiator solution (260 μl of a 20 mg/ml solution in THF) was added via syringe. The vial was sealed and allowed to stir in the glove box for 1 h. An aliquot (20 μl) was removed and analyzed by FTIR to confirm that all the NCA was consumed. In the glove box, α-methoxy-ω-isocyanoethyl-poly(ethylene glycol)$_{45}$ (mPEG$_{23}$-NCO) (20 mg) was dissolved in THF (1 ml) in a 20 ml scintillation vial. An aliquot (350 μl) of the polymerization solution containing active chain ends was removed and added to the solution of mPEG$_{23}$-NCO. The PEG end-capped sample (MA$_x$-mPEG$_{23}$) was sealed, allowed to stir for 24 h, and then used for chain length determination (vide infra). Separately, aliquots of the polymerization solution containing active chains (1.2 ml each) were added to vials containing either Bn-Glu NCA (32 mg, 0.12 mmol) or TFA-Lys NCA (33 mg, 0.12 mmol) dissolved in THF (64 μl or 65 μl, respectively). The vials were sealed and allowed to stir in the glove box for 1 h to give the diblock copolypeptides, (MA)$_{155}$(TFA-K)$_{60}$ (SEQ ID NO: 27) and (MA)$_{155}$(Bn-E)$_{60}$ (SEQ ID NO: 26). FTIR was used to confirm complete consumption of NCAs in both reactions. Outside the glove box, the block copolypeptide solutions were precipitated into 10 mM HCl (20 ml), and then washed with 10 mM aqueous HCl (2×20 ml) to remove residual cobalt ions. The white precipitates were then washed with DI water (3×20 ml) and freeze-dried (average yield=98%).

Analytical data: (MA)$_{155}$(Bn-E)$_{60}$ (SEQ ID NO: 26)
$^1$H NMR (400 MHz, d-TFA, 25° C.): δ 7.38 (br m, 2.3H), 5.24 (br m, 0.93H), 4.97 (br s, 1H), 4.81 (br m, 0.54H), 2.81 (br m, 2H), 2.6 (br m, 1.06H), 2.40-2.05 (br m, 6.37H), 1.61 (br s, 0.42H). FTIR (THF, 25° C.): 1738 cm$^{-1}$ (benzyl ester), 1652 cm$^{-1}$ (amide I), 1550 cm$^{-1}$ (amide II).

Analytical data: (MA)$_{155}$(TFA-K)$_{60}$ (SEQ ID NO: 27)
$^1$H NMR (400 MHz, d-TFA, 25° C.): δ 4.86 (br s, 0.94H), 4.60 (br m, 0.54H), 3.46 (br m, 1.23H), 2.69 (br m, 2H), 2.17 (br m, 5H), 1.9 (br m, 1.42H), 1.69 (br m, 1.34H), 1.50 (br m, 1.32H), 1.31 (br m, 0.68H). FTIR (THF, 25° C.): 1726 cm$^{-1}$ (TFA amide), 1652 cm$^{-1}$ (amide I), 1550 cm$^{-1}$ (amide II).

Sample Procedure for MA$_x$ Chain Length Determination Using End-Group Analysis

Outside of the glove box, the PEG end-capped sample (MA$_x$-mPEG$_{23}$) from above was washed with 10 mM aqueous HCl (2×). After stirring for 1 h, MA$_x$-mPEG$_{23}$ was collected by centrifugation and washed with DI water (3×20 ml) to remove all non-conjugated mPEG$_{23}$-NCO. The remaining MA$_x$-mPEG$_{23}$ was then freeze-dried to remove residual H$_2$O. To determine MA$_x$ molecular weights (M$_n$), $^1$H NMR spectra were obtained. Since it has been shown that end-capping is quantitative for (PMe$_3$)$_4$Co initiated NCA polymerizations when excess isocyanate is used, integrations of methionine (δ 2.70) and alanine (δ 1.52) resonances versus the polyethylene glycol resonance at δ 3.92 could be used to obtain both M to A ratios and MA$_x$ lengths (found: x=156, designated as MA$_{155}$). $^1$H NMR (400 MHZ, d-TFA, 25° C.): 4.87 (br s, 1H), 4.68 (br s, 0.167H), 3.92 (br m, 0.71H), 2.70 (br m, 2.03H), 2.30-2.05 (br m, 5.16H), 1.52 (br s, 0.43H).

Example 1—Preparation of poly(L-methionine sulfoxide$_{0.88}$-stat-L-alanine$_{0.12}$)$_{155}$-block-poly(ε-trifluoroacetyl-L-lysine)$_{60}$ (SEQ ID NO: 28), (M$^O$A)$_{155}$(TFA-K)$_{60}$ (SEQ ID NO: 29), and poly(L-methionine sulfoxide$_{0.88}$-stat-L-alanine$_{0.12}$)$_{155}$-block-poly(γ-benzyl-L-glutamate)$_{60}$ (SEQ ID NO: 30), (M$^O$A)$_{155}$(Bn-E)$_{60}$ (SEQ ID NO: 31)

In separate scintillation vials (5 ml) containing stir bars, (MA)$_{155}$(TFA-K)$_{60}$ (SEQ ID NO: 27) and (MA)$_{155}$(Bn-E)$_{60}$ (SEQ ID NO: 26) were suspended in 80% tert-butyl hydroperoxide (TBHP) in water (16 eq TBHP per methionine residue). Camphorsulfonic acid (0.2 eq per methionine residue) was then added to each vial, and DI water was added to give final copolymer concentrations of ca. 20 mg/ml. These reactions were stirred for 16 h at ambient temperature (ca. 22° C.). Saturated sodium thiosulfate (0.5 ml) was then added dropwise to each vial in order to quench the reactions, and the samples were transferred to 2000 MWCO dialysis tubes and then dialyzed against DI water for 2 d with frequent water changes. The resulting solutions were freeze-dried to yield white fluffy solids (average yield=97%).

Analytical Data: $(M^O A)_{155}(Bn-E)_{60}$ (SEQ ID NO: 31)
$^1$H NMR (400 MHZ, d-TFA, 25° C.): δ 7.24 (br m, 2.2H), 5.10 (br m, 0.91H), 4.85 (br s, 1H), 4.69 (br m, 0.55H), 3.45-3.10 (br m, 2.06H), 2.90 (br m, 3H), 2.62 (br m, 1.04H), 2.47 (br m, 1.86H), 2.18 (br m, 0.45H), 1.97 (br m, 0.45), 1.49 (br s, 0.40H).

Analytical Data: $(M^O A)_{155}(TFA-K)_{60}$ (SEQ ID NO: 29)
$^1$H NMR (400 MHZ, d-TFA, 25° C.): δ 4.91 (br s, 1H), 4.64 (br m, 0.52H), 3.52-3.10 (br m, 2.96H), 2.96 (br m, 3.03H), 2.67 (br m, 1.04H), 2.46 (br m, 1H), 1.96 (br m, 0.86H), 1.73 (br m, 0.88H), 1.54 (br m, 1.27H).

Example 2—Preparation of poly(L-methionine sulfoxide$_{0.88}$-stat-L-alanine$_{0.12}$)$_{155}$-block-poly(L-lysine)$_{60}$ (SEQ ID NO: 32), $(M^O A)_{155}K_{60}$ (SEQ ID NO: 1)

A sample of $(M^O A)_{155}(TFA-K)_{60}$ (SEQ ID NO: 29) was dispersed in a 9:1 methanol:water mixture (20 mg/ml) and $K_2CO_3$ (2 eq per lysine residue) was added. The reaction was stirred for 8 h at 50° C., and the majority of the methanol was then removed under vacuum. The resulting solution (ca. 10% of original volume) was then diluted with water (3 times the remaining volume), transferred to a 2000 MWCO dialysis bag, and then dialyzed against 0.10 M aqueous NaCl at pH 3 (HCl) for 24 h, followed by DI water for 48 hours with water changes twice per day. The contents of the dialysis bag were then lyophilized to dryness to give a white solid (yield=93%).$^1$ $^1$H NMR (400 MHZ, $D_2O$, 25° C.): δ 4.52 (br s, 1H), 4.37 (br m, 0.52H), 3.2-2.8 (br m, 3.18H), 2.75 (br m, 3.1H), 2.40-2.20 (br m, 2.2H), 1.73 (br m, 1.62H), 1.44 (br m, 1.32H). ATR-IR (25° C.): 1653 cm$^{-1}$ (amide I), 1546 cm$^{-1}$ (amide II).

Example 3—Preparation of poly(L-methionine sulfoxide$_{0.88}$-stat-L-alanine$_{0.12}$)$_{155}$-block-poly(L-glutamate)$_{60}$ (SEQ ID NO: 33), $(M^O A)_{155}E_{60}$ (SEQ ID NO: 2)

A sample of $(M^O A)_{155}(Bn-E)_{60}$ (SEQ ID NO: 31) was dissolved in trifluoroacetic acid (TFA, 30 eq per benzyl glutamate residue) in an ice bath. Methanesulfonic acid (MSA, 35 eq) and anisole (5 eq) were then added under vigorous stirring. The reaction mixture was stirred for 20 min in the ice bath, and then for an additional 90 min at ambient temperature. Next, the copolymer was precipitated using $Et_2O$ (20 ml) and collected by centrifugation. The pellet was dissolved in 10% aqueous $NaHCO_3$ (3 ml), extensively dialyzed (2000 MWCO) against DI water for 2 d, and then freeze-dried to give a white solid (yield=95%).$^4$ $^1$H NMR (400 MHZ, $D_2O$, 25° C.): δ 4.50 (br s, 1H), 4.40 (br m, 0.57H), 3.00 (br m, 2.03H), 2.75 (br m, 2.95H), 2.40-2.10 (br m, 3H), 2.10-1.80 (br m, 1H), 1.44 (br s, 0.4H). ATR-IR (25° C.): 1653 cm$^{-1}$ (amide I), 1546 cm$^{-1}$ (amide II).

Example 4—Example Synthesis of poly(L-methionine sulfoxide$_{0.90}$-stat-L-alanine$_{0.10}$)$_{98}$, $(M^O_{/0.90}A_{/0.10})_{98}$, Test Copolymer Met NCA (50 mg, 0.29 mmol) and Ala NCA (3.3 mg, 0.029 mmol) were dissolved together in THF (50 mg/mL) and placed in a 20 ml scintillation vial containing a stir bar. To the vial, $(PMe_3)_4Co$ initiator solution (140 μl of a 20 mg/ml solution in THF) was added via syringe. The vial was sealed and allowed to stir in the glove box for 1 h. An aliquot (20 μl) was removed and analyzed by FTIR to confirm that all the NCA was consumed. In the glove box, mPEG$_{23}$-NCO (20 mg) was dissolved in THF (1 ml) in a 20 ml scintillation vial. An aliquot (350 μl) of the polymerization solution containing active chain ends was removed and added to the solution of mPEG$_{23}$-NCO. The PEG end-capped sample was sealed, allowed to stir for 24 h, and oxidized to give the methionine sulfoxide derivative, $(M^O_{/0.90}A_{/0.10})_{98}$-mPEG$_{23}$, which was then used for chain length determination as described above. The remainder of the polymerization mixture was isolated by precipitation, and then oxidized to the product methionine sulfoxide derivative, $(M^O_{/0.90}A_{/0.10})_{98}$, following standard procedures described above. Copolymers with different M to A ratios were prepared following similar procedures.

Example 5—Preparation of $(MA)_{155}E/K_x$ PIC Hydrogels

Samples of $(M^O A)_{155}E_x$ and $(M^O A)_{155}K_x$ were separately dissolved in a desired aqueous medium (e.g. DI water, 1×PBS, etc.) at a desired concentration (e.g. 2.0, 3.0, or 5.0 wt %). Once each copolymer was fully dissolved, equal volumes of the copolymer solutions were combined in a scintillation vial (2 ml) and vortexed rigorously for 15 s using a Fisher Vortex Genie 2. The concentration of PIC hydrogel was defined as the sum of the concentrations of the two components after mixing, which is essentially the same as the starting concentrations of each component before mixing. The duration of time before gelation occurred (i.e. gelation time) was found to vary from seconds to minutes depending on sample concentration, the ionic strength, and copolymer composition. A "5 second inversion test" was used to initially confirm gel formation. Zhang, S. et al. *Biomacromolecules* 2015, 16, 1331-1340.

Example 6—Rheology Measurements on $(M^O A)_{155}E/K_x$ PIC Hydrogels

A TA Instruments AR 2000 rheometer with a 20 mm parallel plate geometry and solvent trap was used for all measurements. Frequency sweeps were measured at a constant strain amplitude of 0.05. Strain sweeps were measured at a constant frequency of 5 rad/s. All measurements were performed in the linear regime and were repeated 3 times for each hydrogel sample and the results were averaged and plotted. See FIG. 7A, FIG. 7B, FIG. 8A, and FIG. 8B.

TABLE 2

Properties of diblock copolypeptide PIC hydrogels.

| Sample | Concentration (wt %) | G' (Pa) | G" (Pa) | Clarity |
|---|---|---|---|---|
| $(M^\circ A)_{155}E/K_{30}$ | 5.0 | 30 | 4 | translucent |
| $(M^\circ A)_{155}E/K_{90}$ | 5.0 | 99 | 7 | opaque |
| $(M^\circ A)_{155}E/K_{120}$ | 5.0 | 197 | 15 | opaque |
| $(M^\circ A)_{155}E/K_{60}$ | 2.0 | 3 | 0.7 | translucent |
| $(M^\circ A)_{155}E/K_{60}$ | 3.0 | 29 | 2 | translucent |
| $(M^\circ A)_{155}E/K_{60}$ | 5.0 | 116 | 9 | translucent |
| $(M^\circ A)_{155}E/K_{60}$ | 7.0 | 484 | 22 | translucent |
| $(M^\circ A)_{155}E/K_{60}$ | 15 | 2280 | 181 | translucent |

Samples were prepared in PBS buffer, 20° C.
G' = storage modulus;
G" = loss modulus.
Values are averages of triplicate runs at 5 rad/s and strain amplitude of 0.05. In general, the standard errors for frequency sweeps were less than 3.5%, while the standard errors for strain sweeps were less than 2.5%.

Example 7—Fluorescent Probe Conjugation to $(M^OA)_{155}E_{60}$ (SEQ ID NO: 2) and $(M^OA)_{155}K_{60}$ (SEQ ID NO: 1) Copolypeptides Tetramethylrhodamine isothiocyanate (TRITC) was conjugated to amine groups of lysine side chains. $(M^OA)_{155}K_{60}$ (SEQ ID NO: 1) (10 mg) was dissolved in pH 10 $H_2O$/NaOH (1 ml) in a scintillation vial (20 ml). TRITC was dissolved in DMSO (1 mg/ml) and added to the 1% (w/v) copolypeptide solution at a 5:1 molar ratio of copolypeptide chains to fluorescent probes. The reaction was allowed to proceed for 24 h at ambient temperature. After TRITC modification, the resulting solution was dialyzed (2000 MWCO) against DI water for 2 d, and then freeze-dried to yield the product as an orange solid. Fluorescein isothiocyanate (FITC) was conjugated onto the N-terminal amine of $(M^OA)_{155}E_{60}$ (SEQ ID NO: 2) using a similar procedure.

Example 8—Laser Scanning Confocal Microscopy (LSCM) of Fluorescently Labeled Hydrogels LSCM images of hydrogels (3.0 wt % in PBS) were taken on a Leica TCS-SP1 MP-Inverted Confocal and Multiphoton Microscope equipped with an argon laser (476 and 488 nm blue lines), a diode (DPSS) laser (561 nm yellow-green line), and a helium-neon laser (633 nm far red line). Fluorescently labeled hydrogel samples were visualized on glass slides with a spacer between the slide and the cover slip (double-sided tape) allowing the self-assembled structures to be minimally disturbed during focusing. A Z-slice thickness of 0.78 µm was used. Sample imaging was performed at the Advanced Light Microscopy/Spectroscopy Center (ALMS) at the UCLA California NanoSystems Institute (CNSI).

Example 9—Cryoelectron Microscopy (cryoEM) of Hydrogels

25 µl of a 2.0 wt % $(M^OA)_{155}E/K_6$ hydrogel in PBS buffer was applied on a glass coverslip to form a flat surface onto which a lacey carbon EM grid was gently placed using a pair of tweezers in order to acquire a thin layer of sample. The EM grid was then plunged into liquid nitrogen-cooled ethane to prepare the grid for cryoEM. The vitrified sample was examined in an FEI TF20 cryoelectron microscope at liquid nitrogen temperature. Low dose cryoEM images were recorded on a CCD camera at 4.4 Å/pixel on the specimen level and a defocus value of about −5 µm. Sample preparation and imaging was performed at the Electron Imaging Center for Nanomachines (EICN) at the UCLA California NanoSystems Institute (CNSI).

Example 10—Viability of Neural Stem Progenitor Cells (NSPCs) Encapsulated in Hydrogels NSPCs were harvested from the brain cortex of postnatal day 2 (P2) mice using procedures described in detail previously. Zhang, S. et al. *ACS Biomater. Sci. Eng.* 2015, 1, 705-717. Tissues around the ventricles were excised, diced with a razor blade and placed in Accumax solution (Innovative Cell Technologies, San Diego, CA) for 1 hour to digest brain tissue extracellular matrix. Cells were dissociated and titrated to obtain a single cell suspension that was then cultured in suspension as neurospheres within neural basal media supplemented with B27 (Thermo Fisher Scientific, Waltham, MA) and 20 ng/ml basic fibroblast growth factor (FGF-2) and epidermal growth factor (EGF) (Peprotech, Rocky Hill, NJ). Growth media was replaced every two days and neurospheres were passaged every four days or as needed. Cell encapsulation within hydrogels was performed by adding an equal volume of dissociated NSPC suspension in cell media (30.000 cells/µl) to a 10 wt % $(M^OA)_{155}E_{60}$ (SEQ ID NO: 2) solution in cell media to give a resulting copolymer concentration of 5.0 wt %. This mixture was rapidly combined with an equal volume of 5.0 wt % $(M^OA)_{155}K_{60}$ (SEQ ID NO: 1) solution in cell media to yield an overall 5.0 wt % cell containing $(M^OA)_{155}E/K_{60}$ hydrogel. In a similar manner, a 4.0 wt % $K_{180}L_{20}$ (SEQ ID NO: 3) hydrogel control sample in cell media was diluted with an equal volume of cell suspension to yield a final hydrogel concentration of 2.0 wt %. A cell suspension alone in media (15,000 cells/µl) without any hydrogel was also used as a control and baseline. For each of these samples, a 20 µl aliquot was deposited on top of 1.0 wt % agarose gel in media within an Eppendorf tube. The samples were stored in an incubator (37° C., 5% $CO_2$) and were removed after 1 day for analysis. The samples were diluted 50 fold with PBS, and the cells were pelleted using a microfuge. The Live/Dead® viability/cytotoxicity assay (Thermo Fisher Scientific, Waltham, MA) was employed to quantify the percentages of NSPCs both alive and dead after hydrogel encapsulation. Samples were incubated with Live/Dead stain (2 µM calcein AM and 4 µM EthD-1 in PBS) for 30 min at room temperature. The samples were examined under a Zeiss fluorescence microscope (Carl Zeiss Inc) with filters separating light emission from calcein (live, green, light color) and EthD-1 (dead, red, darker color). Finally, all the live/dead cells were counted using imageJ. The resulting counts were averaged (6 samples of $(M^OA)_{155}E/K_{60}$ and 5 samples for both cell control and $K_{180}L_{20}$ (SEQ ID NO: 3) and normalized against the cell control.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A hydrogel composition comprising a first diblock copolypeptide consisting essentially of Substructure I, a second diblock copolypeptide consisting essentially of Substructure II, and water,
wherein
Substructure I is depicted as follows:

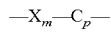  Substructure I;

Substructure II is depicted as follows:

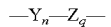  Substructure II;

each instance of X is independently selected from methionine sulfoxide, glycine, and alanine, provided that at least 80 mol % of the X amino acid residues are methionine sulfoxide;
each instance of Y is independently selected from methionine sulfoxide, glycine, and alanine, provided that at least 80 mol % of the Y amino acid residues are methionine sulfoxide;
each instance of C is an amino acid residue independently selected from a cationic amino acid;
each instance of Z is an amino acid residue independently selected from an anionic amino acid;
m is about 100 to about 600;
n is about 100 to about 600;
p is about 20 to about 200;
q is about 20 to about 200;
at least 90 mol % of the C amino acid residues are (D)-amino acid residues or at least 90 mol % of the C amino acid residues are (L)-amino acid residues; and
at least 90 mol % of the Z amino acid residues are (D)-amino acid residues or at least 90 mol % of the Z amino acid residues are (L)-amino acid residues.

2. The composition of claim 1, wherein at least 90 mol % of the X amino acid residues are (D)-amino acid residues or at least 90 mol % of the X amino acid residues are (L)-amino acid residues.

3. The composition of claim 1, wherein each instance of Y is methionine sulfoxide.

4. The composition of claim 1, wherein at least 90 mol % of the Y amino acid residues are (D)-amino acid residues or at least 90% of the Y amino acid residues are (L)-amino acid residues.

5. The composition of claim 1, wherein at least 85 mol % of the Y amino acid residues are methionine sulfoxide.

6. The composition of claim 1, wherein each instance of C is lysine or arginine.

7. The composition of claim 1, wherein each instance of Z is glutamic acid or aspartic acid.

8. The composition of claim 1, wherein m is from about 100 to about 220.

9. The composition of claim 1, wherein n is from about 100 to about 220.

10. The composition of claim 1, wherein p is from about 20 to about 130.

11. The composition of claim 1, wherein q is from about 20 to about 130.

12. The composition of claim 1, wherein the polydispersity of the first diblock copolypeptide or the second diblock copolypeptide is less than 1.5.

13. The composition of claim 1, wherein the number of amino acid residues in the first diblock copolypeptide is from about 90% to about 110% of the number of amino acid residues in the second diblock copolypeptide.

14. A composition comprising water, a first diblock copolypeptide and second diblock copolypeptide, wherein the first diblock copolypeptide is selected from $(M^OA)_{155}K_{30}$ (SEQ ID NO: 7), $(M^OA)_{155}K_{60}$ (SEQ ID NO: 1) $(M^OA)_{155}K_{90}$ (SEQ ID NO: 12), and $(M^OA)_{155}K_{120}$ (SEQ ID NO: 13), and the second diblock copolypeptide is selected from $(M^OA)_{155}E_{30}$ (SEQ ID NO: 10), $(M^OA)_{155}E_{60}$ (SEQ ID NO: 2), $(M^OA)_{155}E_{90}$ (SEQ ID NO: 8), $(M^OA)_{155}E_{120}$ (SEQ ID NO: 11), and $(M^OA)_{155}(rac\text{-}E)_{60}$ (SEQ ID NO: 9); wherein $M^OA$ is L-methionine sulfoxide-stat-L-alanine; and 155 is the total number of amino acids of $M^O$ and A combined.

15. The composition of claim 1, wherein the total concentration of the first diblock copolypeptide and the second diblock copolypeptide in the composition is greater than 2.0 wt. %.

16. The composition of claim 1, wherein the molar ratio of C to Z is from about 0.95 to about 1.05.

17. The composition of claim 1, wherein the molar ratio of X to Y is from about 0.95 to about 1.05.

18. The composition of claim 1, wherein the composition further comprises a salt.

19. The composition of claim 18, wherein the concentration of the salt in the composition is less than 500 mM.

20. The composition of claim 1, wherein the composition further comprises a buffer.

21. The composition of claim 1, wherein each instance of C is independently lysine or arginine and each instance of Z is independently glutamic acid or aspartic acid.

* * * * *